United States Patent
Gray et al.

(10) Patent No.: US 11,180,568 B2
(45) Date of Patent: *Nov. 23, 2021

(54) ANTIBODY THERAPEUTICS THAT BIND CD137

(71) Applicant: Sorrento Therapeutics, Inc., San Diego, CA (US)

(72) Inventors: John Dixon Gray, San Diego, CA (US); Heyue Zhou, San Diego, CA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 16/270,761

(22) Filed: Feb. 8, 2019

(65) Prior Publication Data

US 2019/0161554 A1    May 30, 2019

Related U.S. Application Data

(63) Continuation of application No. 15/049,718, filed on Feb. 22, 2016, now Pat. No. 10,233,251.

(60) Provisional application No. 62/119,211, filed on Feb. 22, 2015.

(51) Int. Cl.
*C07K 16/28* (2006.01)

(52) U.S. Cl.
CPC ...... *C07K 16/2878* (2013.01); *C07K 2317/21* (2013.01); *C07K 2317/33* (2013.01); *C07K 2317/56* (2013.01); *C07K 2317/70* (2013.01); *C07K 2317/75* (2013.01); *C07K 2317/92* (2013.01)

(58) Field of Classification Search
CPC .................. C07K 2317/56; C07K 16/2896
USPC ............................................ 424/133.1, 174.1
See application file for complete search history.

(56) References Cited

U.S. PATENT DOCUMENTS

| | | | | |
|---|---|---|---|---|
| 7,037,498 | B2 * | 5/2006 | Cohen | A61P 35/00 424/156.1 |
| 10,233,251 | B2 * | 3/2019 | Gray | A61P 13/12 |
| 10,259,881 | B2 * | 4/2019 | Gray | A61P 1/16 |
| 2003/0223989 | A1 | 12/2003 | Pluenneke | |
| 2016/0244528 | A1 | 8/2016 | Gray et al. | |
| 2016/0257758 | A1 | 9/2016 | Gray et al. | |
| 2017/0226215 | A1 | 8/2017 | Gray et al. | |
| 2020/0048350 | A1 * | 2/2020 | Eckelman | C07K 16/468 |
| 2020/0190193 | A1 * | 6/2020 | Pandit | C07K 16/2866 |

FOREIGN PATENT DOCUMENTS

| | | |
|---|---|---|
| WO | 2003/049755 A1 | 6/2003 |
| WO | 2005/035584 A1 | 4/2005 |
| WO | 2006/088447 A1 | 8/2006 |
| WO | 2012/032433 A1 | 3/2012 |

OTHER PUBLICATIONS

European Search Report relating to corresponding application: EP 16 75 3215.9, dated Aug. 31, 2018.
Fisher, et al. "Targeting of 4-1BB by monoclonal antibody PF-05082566 enhances T-cell function and promotes anti-tumor activity," Cancer Immunology, Immunotherapy: vol. 61, No. 10, pp. 1721-1733 (Mar. 2012).
Hodge, et al., "Targeting peripheral blood pro-inflammatory cytotoxic lymphocytes by inhibiting CD137 expression: novel potential treatment for COPD," BMC Pulmonary Medicine: vol. 14, pp. 1-11, (2014).
International Preliminary Report on Patentability for International Application No. PCT/2016/018897, dated Aug. 22, 2017.
International Search Report and Written Opinion for International Application No. PCT/US2016/018897, completed on Jul. 1, 2016 and dated Jul. 29, 2016.
Kohrt et al., "Targeting CD137 enhances the efficacy of cetuximab," J. Clin. Invest.: vol. 124, pp. 2668-2682, (2014).
Lederman et al., Molecular Immunology 28:1171-1181 (1991).
Li et al., PNAS 77: 3211-3214 (1980).
Son, J. H., et al., "Humanization of agonistic anti-huamn 4-1BB monoclonal antibody using a phage-displayed combinatorial library," Journal of Immunological Meth, Elsevier Science Publishers B.V. Amsterdam, NL, vol. 286, No. 1-2, pp. 187-201, (Mar. 2004).
Supplemental European Search Report relating to Corresponding European Application No. 16753215.9 / PCT/US2016/018897, completed on May 31, 2018 and dated Jun. 13, 2018.
Zhou, H., et al., Xi Bao Yu Fen Zi Mian Yi Xue Za Zhi; "Preparation of anti-human 4-1BB monoclonal antibody and characterization of its biological activities", NCBI Pub Med.gov, 27 (9): 993-996 Abstract Only, (Sep. 2011).

* cited by examiner

*Primary Examiner* — Lynn A Bristol
(74) *Attorney, Agent, or Firm* — Baker Botts L.L.P.

(57) ABSTRACT

There is disclosed compositions and methods relating to or derived from anti-CD137 antibodies. More specifically, there is disclosed fully human antibodies that bind CD137, CD137-antibody binding fragments and derivatives of such antibodies, and CD137-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease requiring either stimulation of immune responses or suppression. Diseases amenable to treatment is selected from the group consisting of cancers, autoimmune diseases and viral infections.

19 Claims, 5 Drawing Sheets

Specification includes a Sequence Listing.

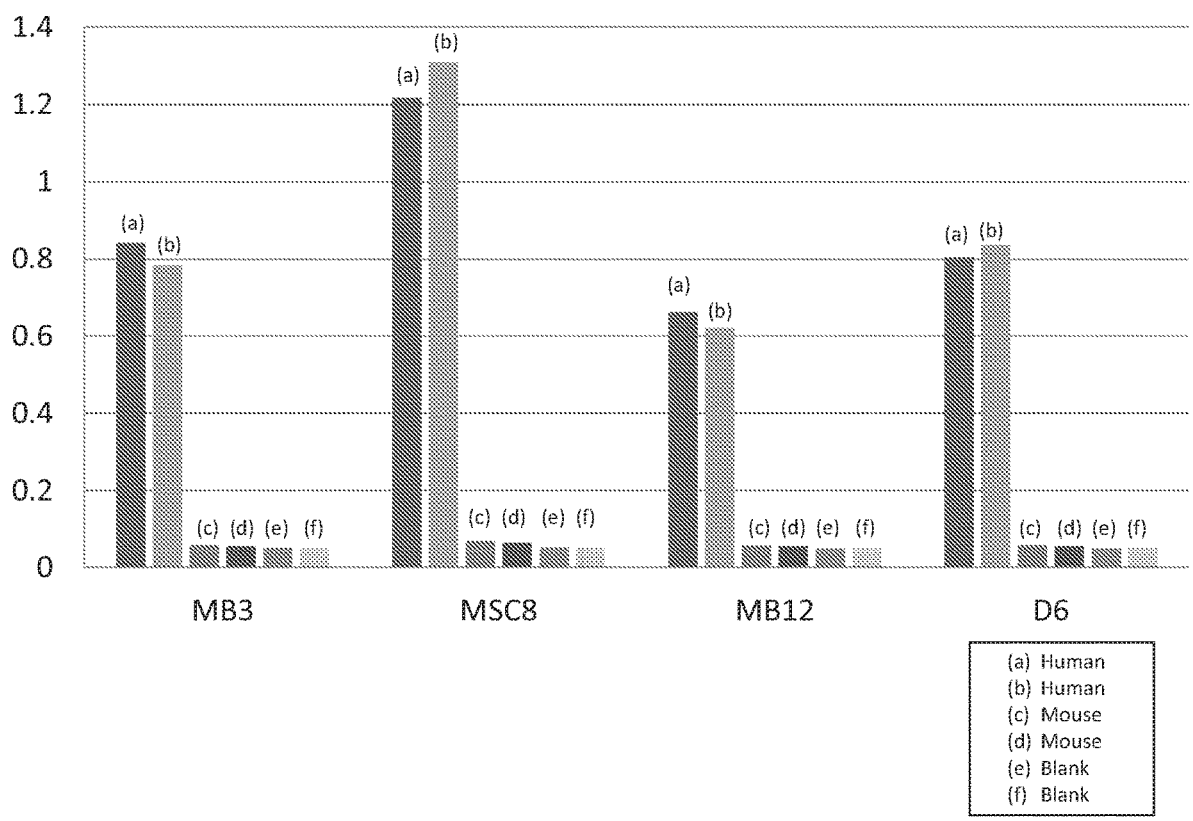

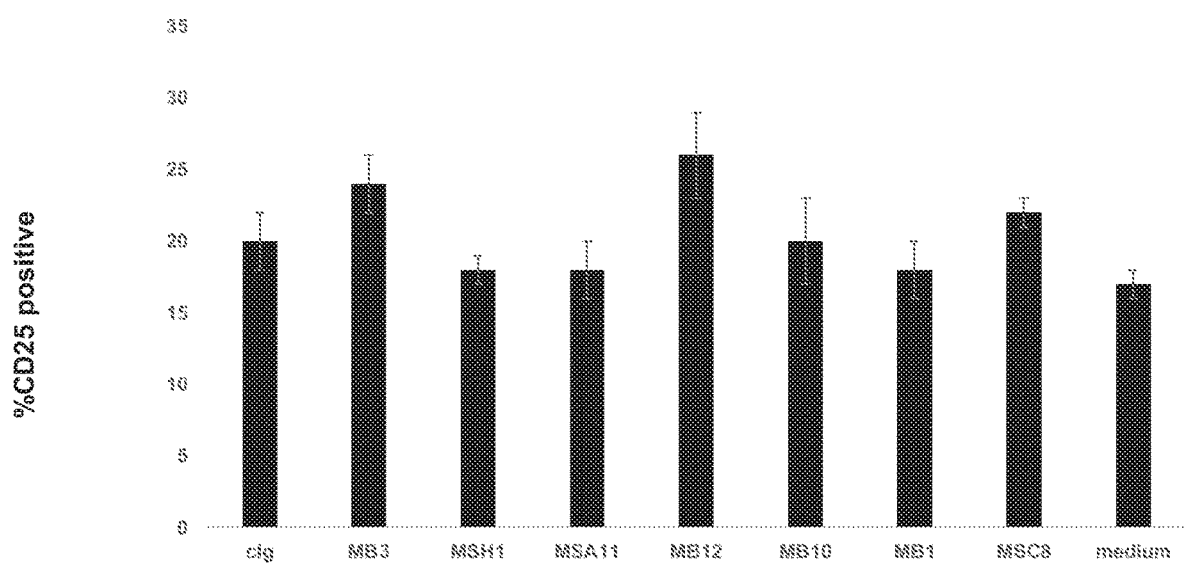

US 11,180,568 B2

ANTIBODY THERAPEUTICS THAT BIND CD137

RELATED APPLICATIONS

This application is a continuation of U.S. patent application Ser. No. 15/049,718, filed on Feb. 22, 2016, now allowed, which claims priority to U.S. Provisional Application No. 62/119,211, filed on Feb. 22, 2015, the entire contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 8, 2019, is named S103014 1390US1.C1.txt and is 160 kilobytes in size.

TECHNICAL FIELD

The present disclosure provides compositions and methods relating to or derived from anti-CD137 antibodies. More specifically, the present disclosure provides fully human antibodies that bind CD137, CD137-antibody binding fragments and derivatives of such antibodies, and CD137-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease requiring either stimulation of immune responses or suppression.

BACKGROUND

CD137 is a member of the tumor necrosis factor (TNF) receptor family. Its alternative names are tumor necrosis factor receptor superfamily member 9 (TNFRSF9), 4-1BB and induced by lymphocyte activation (ILA). CD137 can be expressed by activated T cells, but to a larger extent on CD8 than on CD4 T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion survival and cytolytic activity. Further, it can enhance immune activity to eliminate tumors in mice.

CD137 is a T-cell costimulatory receptor induced on TCR activation (Nam et al., Curr. Cancer Drug Targets, 5:357-363 (2005); Watts et al., Annu. Rev. Immunol., 23:23-68 (2005)). In addition to its expression on activated $CD4^+$ and $CD8^+$ T cells, CD137 is also expressed on $CD4^+$ $CD25^+$ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al., Annu. Rev. Immunol., 23:23-68 (2005)). On interaction with its ligand, CD137 leads to increased TCR-induced T-cell proliferation, cytokine production, functional maturation, and prolonged $CD8^+$ T-cell survival (Nam et al., Curr. Cancer Drug Targets, 5:357-363 (2005), Watts et al., Annu. Rev. Immunol., 23:23-68 (2005)).

Signaling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun NH2-terminal kinase/stress-activated protein kinase (JNK/SAPK), and p38 mitogen-activated protein kinase (MAPK) signaling pathways, and (2) the control of anti-apoptotic and cell cycle-related gene expression. Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity. Furthermore, CD137-stimulated NK cells promote the expansion of activated T cells in vitro. In accordance with their costimulatory function, agonist mAbs against CD137 have been shown to promote rejection of cardiac and skin allografts, eradicate established tumors, broaden primary antiviral CD8+ T cell responses, and increase T cell cytolytic potential. These studies support the view that CD137 signaling promotes T cell function which may enhance immunity against tumors and infection.

Other anti-CD137 antibodies have been disclosed in U.S. 2005/0095244, issued U.S. Pat. No. 7,288,638 (such as 20H4.9-IgG4 [10C7 or BMS-663513] or 20H4.9-IgG1 [BMS-663031]); U.S. Pat. No. 6,887,673 [4E9 or BMS-554271]; 7,214,493; 6,303,121; 6,569,997; 6,905,685; 6,355,476; 6,362,325 [1D8 or BMS-469492; 3H3 or BMS-469497; or 3E1]; U.S. Pat. No. 6,974,863 (such as 53A2); or U.S. Pat. No. 6,210,669 (such as 1D8, 3B8, or 3E1). Additional CD137 agonistic antibodies are described in U.S. Pat. Nos. 5,928,893; 6,303,121 and 6,569,997.

These and other deficiencies in the previous antibodies are overcome by the provision of fully human antibodies to CD137 by the present disclosure.

SUMMARY

The present disclosure provides a fully human anti-CD137 antibody of an IgG class that binds to a CD137 epitope with a binding affinity of at least $10^{-6}$M, which comprises a heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO.

129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, SEQ ID NO. 143, and comprises a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128.

In one embodiment, the fully human antibody comprises both a heavy chain and a light chain variable domain sequence selected from the group consisting of SEQ ID NO. 1/SEQ ID NO. 2 (called A1 herein), SEQ ID NO. 3/SEQ ID NO. 4 (called A4 herein), SEQ ID NO. 5/SEQ ID NO. 6 (called A11 herein), SEQ ID NO. 7/SEQ ID NO. 8 (called B1 herein), SEQ ID NO. 9/SEQ ID NO. 10 (called B3 herein), SEQ ID NO. 11/SEQ ID NO. 12 (called B12 herein), SEQ ID NO. 13/SEQ ID NO. 14 (called C2 herein), SEQ ID NO. 15/SEQ ID NO. 16 (called C3 herein), SEQ ID NO. 17/SEQ ID NO. 18 (called C7 herein), SEQ ID NO. 19/SEQ ID NO. 20 (called C11 herein), SEQ ID NO. 21/SEQ ID NO. 22 (called C12 herein), SEQ ID NO. 23/SEQ ID NO. 24 (called D1 herein), SEQ ID NO. 25/SEQ ID NO. 26 (called D4 herein), SEQ ID NO. 27/SEQ ID NO. 28 (called D6 herein), SEQ ID NO. 29/SEQ ID NO. 30 (called D7 herein), SEQ ID NO. 31/SEQ ID NO. 32 (called D8 herein), SEQ ID NO. 33/SEQ ID NO. 34 (called D10 herein), SEQ ID NO. 35/SEQ ID NO. 36 (called E2 herein), SEQ ID NO. 37/SEQ ID NO. 38 (called ES herein), SEQ ID NO. 39/SEQ ID NO. 40 (called E7 herein), SEQ ID NO. 41/SEQ ID NO. 42 (called F5 herein), SEQ ID NO. 43/SEQ ID NO. 44 (called F7 herein), SEQ ID NO. 45/SEQ ID NO. 46 (called F11 herein), SEQ ID NO. 47/SEQ ID NO. 48 (called G1 herein), SEQ ID NO. 49/SEQ ID NO. 50 (called G2 herein), SEQ ID NO. 51/SEQ ID NO. 52 (called G3 herein), SEQ ID NO. 53/SEQ ID NO. 54 (called G5 herein), SEQ ID NO. 55/SEQ ID NO. 56 (called G6 herein), SEQ ID NO. 57/SEQ ID NO. 58 (called G8 herein), SEQ ID NO. 59/SEQ ID NO. 60 (called G12 herein), SEQ ID NO. 61/SEQ ID NO. 62 (called H4 herein), SEQ ID NO. 63/SEQ ID NO. 64 (called H7 herein), SEQ ID NO. 65/SEQ ID NO. 66 (called H8 herein), SEQ ID NO. 67/SEQ ID NO. 68 (called H10 herein), SEQ ID NO. 69/SEQ ID NO. 70 (called H11 herein), SEQ ID NO. 71/SEQ ID NO. 72 (called C3sh1A1 herein), SEQ ID NO. 73/SEQ ID NO. 74 (called C3sh1A2 herein), SEQ ID NO. 75/SEQ ID NO. 76 (called C3sh1A5 herein), SEQ ID NO. 77/SEQ ID NO. 78 (called C3sh1A9 herein), SEQ ID NO. 79/SEQ ID NO. 80 (called C3sh1B2 herein), SEQ ID NO. 81/SEQ ID NO. 82 (called C3sh1B4 herein), SEQ ID NO. 83/SEQ ID NO. 84 (called C3sh1B6 herein), SEQ ID NO. 85/SEQ ID NO. 86 (called C3sh1B9 herein), SEQ ID NO. 87/SEQ ID NO. 88 (called C3sh1C1 herein), SEQ ID NO. 89/SEQ ID NO. 90 (called C3sh1C2 herein), SEQ ID NO. 91/SEQ ID NO. 92 (called C3sh1C7 herein), SEQ ID NO. 93/SEQ ID NO. 94 (called C3sh1D1 herein), SEQ ID NO. 95/SEQ ID NO. 96 (called C3sh1D4 herein), SEQ ID NO. 97/SEQ ID NO. 98 (called C3sh1D6 herein), SEQ ID NO. 99/SEQ ID NO. 100 (called C3sh1E2 herein), SEQ ID NO. 101/SEQ ID NO. 102 (called C3sh1E7 herein), SEQ ID NO. 103/SEQ ID NO. 104 (called C3sh1E9 herein), SEQ ID NO. 105/SEQ ID NO. 106 (called C3sh1F1 herein), SEQ ID NO. 107/SEQ ID NO. 108 (called C3sh1F10 herein), SEQ ID NO. 109/SEQ ID NO. 110 (called C3sh1F12 herein), SEQ ID NO. 111/SEQ ID NO. 112 (called C3sh1F2 herein), SEQ ID NO. 113/SEQ ID NO. 114 (called C3sh1G1 herein), SEQ ID NO. 115/SEQ ID NO. 116 (called C3sh1G11 herein), SEQ ID NO. 117/SEQ ID NO. 118 (called C3sh1G2 herein), SEQ ID NO. 119/SEQ ID NO. 120 (called C3sh1G3 herein), SEQ ID NO. 121/SEQ ID NO. 122 (called C3sh1G5 herein), SEQ ID NO. 123/SEQ ID NO. 124 (called C3sh1G8 herein), SEQ ID NO. 125/SEQ ID NO. 126 (called C3sh1H10 herein), SEQ ID NO. 127/SEQ ID NO. 128 (called C3sh1H4 herein), SEQ ID NO. 129/SEQ ID NO. 28 (called MA8 herein), SEQ ID NO. 130/SEQ ID NO. 28 (called MB1 herein), SEQ ID NO. 131/SEQ ID NO. 28 (called MB3 herein), SEQ ID NO. 132/SEQ ID NO. 28 (called MB10 herein), SEQ ID NO. 133/SEQ ID NO. 28 (called MB12 herein), SEQ ID NO. 134/SEQ ID NO. 28 (called MC8 herein), SEQ ID NO. 135/SEQ ID NO. 28 (called MD1 herein), SEQ ID NO. 136/SEQ ID NO. 28 (called MD4 herein), SEQ ID NO. 137/SEQ ID NO. 28 (called MSA11 herein), SEQ ID NO. 138/SEQ ID NO. 28 (called MSB7 herein), SEQ ID NO. 139/SEQ ID NO. 28 (called MSD2 herein), SEQ ID NO. 140/SEQ ID NO. 28 (called MSE3 herein), SEQ ID NO. 141/SEQ ID NO. 28 (called MSE5 herein), SEQ ID NO. 142/SEQ ID NO. 28 (called MSC8 herein), and SEQ ID NO. 143/SEQ ID NO. 28 (called MSH1 herein).

The present disclosure provides an anti-CD47 fully human antibody fragment, comprising a heavy chain variable domain comprising an amino acid sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, and SEQ ID NO. 143, and a light chain variable domain comprising an amino acid sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128, wherein the fragment is a single chain antibody comprising a peptide linker connecting the heavy and light chain variable domains, or a Fab fragment.

In one embodiment, the fully human antibody fragment comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 139/SEQ ID NO. 28, SEQ ID NO. 140/SEQ ID NO. 28, SEQ ID NO. 141/SEQ ID NO. 28, SEQ ID NO. 142/SEQ ID NO. 28, and SEQ ID NO. 143/SEQ ID NO. 28.

The present disclosure further provides a method of treating cancer in a subject in need thereof, comprising administering an effective amount of an antibody of any one of the above aspects or embodiments, such that the cancer is treated.

In one embodiment, the cancer is selected from the group consisting of ovarian cancer, colorectal cancer, melanoma, hepatocellular carcinoma, renal cancer, breast cancer, head and neck cancer, lung cancer and liver cancer.

The present disclosure also provides a method for treating a disease requiring either stimulation of an immune response or suppression, comprising administering an effective amount of the antibody or antibody fragment of any one of the above aspects or embodiments.

In one embodiment, the antibody or antibody fragment comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 139/SEQ ID NO. 28, SEQ ID NO. 140/SEQ ID NO. 28, SEQ ID NO. 141/SEQ ID NO. 28, SEQ ID NO. 142/SEQ ID NO. 28, and SEQ ID NO. 143/SEQ ID NO. 28.

Preferably, the disease is selected from the group consisting of cancers, autoimmune diseases and viral infections.

In one embodiment, the invention includes an isolated anti-CD137 antibody, or an antigen-binding fragment thereof, comprising a heavy chain variable domain comprising complementarity determining regions (CDRs) as set forth in a heavy chain variable domain amino acid sequence selected from the group consisting of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 138, 139, 140, 141, 142 and 143; and comprising a light chain variable domain comprising CDRs as set forth in a light chain variable region amino acid sequence selected from the group consisting of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128.

In one embodiment, the isolated anti-CD137 antibody, or an antigen-binding fragment thereof, comprises both a heavy chain and a light chain variable domain sequence selected from the group consisting of SEQ ID NO. 1/SEQ ID NO. 2 (called A1 herein), SEQ ID NO. 3/SEQ ID NO. 4 (called A4 herein), SEQ ID NO. 5/SEQ ID NO. 6 (called A11 herein), SEQ ID NO. 7/SEQ ID NO. 8 (called B1 herein), SEQ ID NO. 9/SEQ ID NO. 10 (called B3 herein), SEQ ID NO. 11/SEQ ID NO. 12 (called B12 herein), SEQ ID NO. 13/SEQ ID NO. 14 (called C2 herein), SEQ ID NO. 15/SEQ ID NO. 16 (called C3 herein), SEQ ID NO. 17/SEQ ID NO. 18 (called C7 herein), SEQ ID NO. 19/SEQ ID NO. 20 (called C11 herein), SEQ ID NO. 21/SEQ ID NO. 22 (called C12 herein), SEQ ID NO. 23/SEQ ID NO. 24 (called D1 herein), SEQ ID NO. 25/SEQ ID NO. 26 (called D4 herein), SEQ ID NO. 27/SEQ ID NO. 28 (called D6 herein), SEQ ID NO. 29/SEQ ID NO. 30 (called D7 herein), SEQ ID NO. 31/SEQ ID NO. 32 (called D8 herein), SEQ ID NO. 33/SEQ ID NO. 34 (called D10 herein), SEQ ID NO. 35/SEQ ID NO. 36 (called E2 herein), SEQ ID NO. 37/SEQ ID NO. 38 (called ES herein), SEQ ID NO. 39/SEQ ID NO. 40 (called E7 herein), SEQ ID NO. 41/SEQ ID NO. 42 (called F5 herein), SEQ ID NO. 43/SEQ ID NO. 44 (called F7 herein), SEQ ID NO. 45/SEQ ID NO. 46 (called F11 herein), SEQ ID NO. 47/SEQ ID NO. 48 (called G1 herein), SEQ ID NO. 49/SEQ ID NO. 50 (called G2 herein), SEQ ID NO. 51/SEQ ID NO. 52 (called G3 herein), SEQ ID NO. 53/SEQ ID NO. 54 (called G5 herein), SEQ ID NO. 55/SEQ ID NO. 56 (called G6 herein), SEQ ID NO. 57/SEQ ID NO. 58 (called G8 herein), SEQ ID NO. 59/SEQ ID NO. 60 (called G12 herein), SEQ ID NO. 61/SEQ ID NO. 62 (called H4 herein), SEQ ID NO. 63/SEQ ID NO. 64 (called H7 herein), SEQ ID NO. 65/SEQ ID NO. 66 (called H8 herein), SEQ ID NO. 67/SEQ ID NO. 68 (called H10 herein), SEQ ID NO. 69/SEQ ID NO. 70 (called H11 herein), SEQ ID NO. 71/SEQ ID NO. 72 (called C3sh1A1 herein), SEQ ID NO. 73/SEQ ID NO. 74 (called C3sh1A2 herein), SEQ ID NO. 75/SEQ ID NO. 76 (called C3sh1A5 herein), SEQ ID NO. 77/SEQ ID NO. 78 (called C3sh1A9 herein), SEQ ID NO. 79/SEQ ID NO. 80 (called C3sh1B2 herein), SEQ ID NO. 81/SEQ ID NO. 82 (called C3sh1B4 herein), SEQ ID NO. 83/SEQ ID NO. 84 (called C3sh1B6 herein), SEQ ID NO. 85/SEQ ID NO. 86 (called C3sh1B9 herein), SEQ ID NO. 87/SEQ ID NO. 88 (called C3sh1C1 herein), SEQ ID NO. 89/SEQ ID NO. 90 (called C3sh1C2 herein), SEQ ID NO. 91/SEQ ID NO. 92 (called C3sh1C7 herein), SEQ ID NO. 93/SEQ ID NO. 94 (called C3sh1D1 herein), SEQ ID NO. 95/SEQ ID NO. 96 (called C3sh1D4 herein), SEQ ID NO. 97/SEQ ID NO. 98 (called C3sh1D6 herein), SEQ ID NO. 99/SEQ ID NO. 100 (called C3sh1E2 herein), SEQ ID NO. 101/SEQ ID NO. 102 (called C3sh1E7 herein), SEQ ID NO. 103/SEQ ID NO. 104 (called C3sh1E9 herein), SEQ ID NO. 105/SEQ ID NO. 106 (called C3sh1F1 herein), SEQ ID NO. 107/SEQ ID NO. 108 (called C3sh1F10 herein), SEQ ID NO. 109/SEQ ID NO. 110 (called C3sh1F12 herein), SEQ ID NO. 111/SEQ ID NO. 112 (called C3sh1F2 herein), SEQ ID NO. 113/SEQ ID NO. 114 (called C3sh1G1 herein), SEQ ID NO. 115/SEQ ID NO. 116 (called C3sh1G11 herein), SEQ ID NO. 117/SEQ ID NO. 118 (called C3sh1G2 herein), SEQ ID NO. 119/SEQ ID NO. 120 (called C3sh1G3 herein), SEQ ID NO. 121/SEQ ID NO. 122 (called C3sh1G5 herein), SEQ ID NO. 123/SEQ ID NO. 124 (called C3sh1G8 herein), SEQ ID NO. 125/SEQ ID NO. 126 (called C3sh1H10 herein), SEQ ID NO. 127/SEQ ID NO. 128 (called C3sh1H4 herein), SEQ ID NO. 129/SEQ ID NO. 28 (called MA8 herein), SEQ ID NO. 130/SEQ ID NO. 28 (called MB1 herein), SEQ ID NO. 131/SEQ ID NO. 28 (called MB3 herein), SEQ ID NO. 132/SEQ ID NO. 28 (called MB10 herein), SEQ ID NO. 133/SEQ ID NO. 28 (called MB12 herein), SEQ ID NO. 134/SEQ ID NO. 28 (called MC8 herein), SEQ ID NO. 135/SEQ ID NO. 28 (called MD1 herein), SEQ ID NO. 136/SEQ ID NO. 28 (called MD4 herein), SEQ ID NO. 137/SEQ ID NO. 28 (called MSA11 herein), SEQ ID NO. 138/SEQ ID NO. 28 (called MSB7 herein), SEQ ID NO. 139/SEQ ID NO. 28 (called MSD2 herein), SEQ ID NO. 140/SEQ ID NO. 28 (called MSE3 herein), SEQ ID NO. 141/SEQ ID NO. 28 (called MSE5 herein), SEQ ID NO. 142/SEQ ID NO. 28 (called MSC8 herein), and SEQ ID NO. 143/SEQ ID NO. 28 (called MSH1 herein).

In certain embodiments, the anti-CD137 antibody, or antigen-binding fragment thereof, of the invention has a $K_D$ of at least $1 \times 10^{-6}$M. In other embodiments, the anti-CD137 antibody, or antigen-binding fragment thereof, of the invention has a $K_D$ of at least $1 \times 10^{-7}$M. In other embodiments, the anti-CD137 antibody, or antigen-binding fragment thereof, of the invention has a $K_D$ of at least $1 \times 10^{-8}$M.

The invention also provides pharmaceutical compositions comprising an effective amount of an anti-CD137 antibodies or fragments disclosed herein, and a pharmaceutically acceptable carrier.

In certain embodiments, the invention features a method of treating cancer in a human subject in need thereof, comprising administering an effective amount of an anti-CD137 antibody, or antigen-binding fragment thereof, disclosed herein to the subject, such that cancer is treated. Examples of cancer that may be treated include, but are not limited to, ovarian cancer, colorectal cancer, melanoma, hepatocellular carcinoma, renal cancer, breast cancer, head and neck cancer, lung cancer and liver cancer.

DESCRIPTION OF THE DRAWINGS

FIG. 2 graphically depicts cross-reactivity studies determining whether anti-CD137 antibodies D6, MB3, MSC8, and MB12 are able to bind human and/or murine CD137. The results show that each of these antibodies is specific for human CD137, as none of the antibodies showed cross-reactivity to murine CD137.

FIG. 3A and FIG. 3B graphically depict results from an in vitro experiment determining cell activation. The percentage of cells positive for CD25 expression was measured by flow cytometry. The level of CD25 expression was higher in the cultures where anti-CD137 antibodies had been added. FIG. 3B provides the normalized results of FIG. 3A. cIg is a control immunoglobulin which is not specific for CD137.

DETAILED DESCRIPTION

Definitions

Figure 1A:
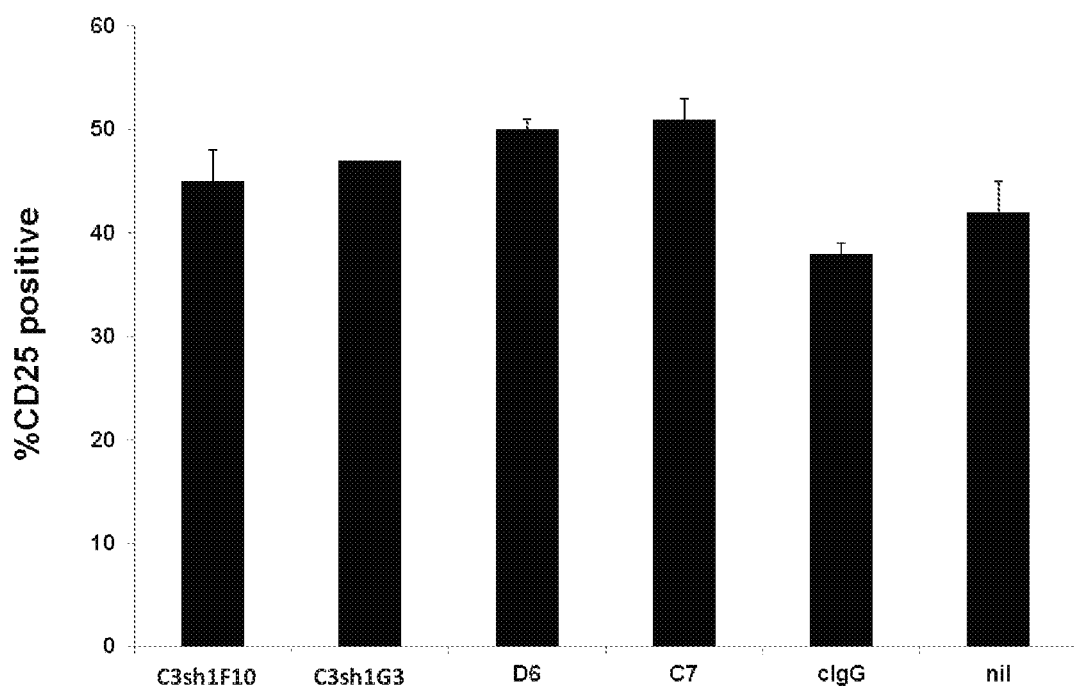
FIG. 1A is a graph that shows functional activity of the listed anti-CD137 antibodies by their ability to augment T cell activation. To measure cell activation, the cells were labeled with FITC anti-human CD25 after three days of culture. The percentage of cells positive for CD25 expression was measured by flow cytometry. The level of CD25 expression was higher in the cultures where anti-CD137 antibodies had been added. cIg is a control immunoglobulin which is not specific for CD137.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, a variant of an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of an immunoglobulin. An "immunoglobulin" is a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT™ (international ImMunoGeneTics information system; Lefranc et al, Dev. Comp. Immunol. 29:185-203; 2005) and AHo (Honegger and Pluckthun, J. Mol. Biol. 309(3):657-670; 2001).

An "antibody" refers to an intact immunoglobulin or to an antigen binding portion thereof that competes with the intact antibody for specific binding, unless otherwise specified. In one embodiment, an antibody comprises a heavy chain variable domain, a light chain variable domain, a light chain constant region ($C_L$), and heavy chain constant regions $C_{H1}$, $C_{H2}$ and $C_{H3}$. The heavy and light chain variable domain sequences may be selected from those described herein in SEQ ID Nos: 1 to 143.

Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

In certain embodiments, antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific."

The term "monospecific", as used herein, refers to an antibody that displays an affinity for one particular epitope. Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody fragment" or "antigen binding fragment of an antibody" comprises a portion of an intact antibody, and preferably comprises the antibody antigen binding or variable domains. Examples of an antibody fragment include a Fab, an Fab', an F(ab')2, an Fv fragment, and a linear antibody.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub. 20/0202512; 2004/0202995; 2004/0038291; 2004/0009507; 2003/0039958, and Ward et al., Nature 341: 544-546, 1989).

A single-chain antibody (scFv) is an antibody fragment in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, *Proc. Natl. Acad. Sci. USA* 85:5879-83).

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An antigen binding protein, such as an antibody, may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains of the antibody are derived from human immunoglobulin sequences (referred to as a "fully human antibody"). These antibodies may be prepared in a variety of ways, examples of which are described below, including through the immunization with an antigen of interest of a mouse that is genetically modified to express antibodies derived from human heavy and/or light chain-encoding genes. In a preferred embodiment, a fully human antibody is made using recombinant methods such that the glycosylation pattern of the antibody is different than an antibody having the same sequence if it were to exist in nature.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immuno specific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CD137 antibody. In another embodiment, all of the CDRs are derived from a human anti-CD137 antibody. In another embodiment, the CDRs from more than one human anti-CD137 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-CD137 antibody, and the CDRs from the heavy chain from a third anti-CD137 antibody. Other combinations are possible.

Further, the framework regions may be derived from one of the same anti-CD137 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind CD137).

An "agonist antibody" as used herein, is an antibody that induces or increases the biological activity of an antigen (for example, CD137) to which the antibody binds. An agonist may, for example, facilitate a receptor's phosphorylation due to binding of the receptor to a ligand or may activate or grow cells activated by the receptor. In one embodiment, the antibodies of the invention are agonist anti-CD137 antibodies.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CD137) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or possibly more than one expression vector, e.g., two expression vectors) comprising at least the coding sequence of the antibody, where said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof, that binds CD137, which is sufficient to effect treatment, prognosis or diagnosis of a disease associated with CD137 dependent signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material and/or chemicals. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

CD137 Antigen Binding Proteins

The present invention pertains to CD137 binding proteins, particularly anti-CD137 antibodies, or antigen-binding portions thereof, that bind CD137, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human CD137, to stimulate CD137 activity, either in vitro or in vivo, and to prevent or treat disorders such as cancer are also encompassed by the invention.

As described in Table 5 below, included in the invention are novel antibody heavy and light chain variable regions that are specific to CD137. In one embodiment, the invention provides an anti-CD137 antibody, or an antigen-binding fragment thereof, that comprises a heavy chain having a variable domain comprising an amino acid sequence as set forth in any one of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 138, 139, 140, 141, 142 and 143. In one embodiment, the invention provides an anti-CD137 antibody, or an antigen-binding fragment thereof, that comprises a light chain having a variable domain comprising an amino acid sequence as set forth in any one of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128. In one embodiment, the invention provides an anti-CD137 antibody, or an antigen-binding fragment thereof, that comprises a light chain having a variable domain comprising an amino acid sequence as set forth in any one of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128; and a heavy chain having a variable domain comprising an amino acid sequence as set forth in any one of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 138, 139, 140, 141, 142 and 143.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present invention provides an anti-CD137 antibody comprising the CDRs of the heavy and light chain variable domains described in Table 5 (SEQ ID Nos: 1 to 143). For example, the invention provides an anti-CD137 antibody, or antigen-binding fragment thereof, comprising a heavy chain variable region having the CDRs described in an amino acid sequence as set forth in any one of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 139, 140, 141, 142 and 143. In one embodiment, the invention provides an anti-CD137 antibody, or antigen-binding fragment thereof, comprising a light chain variable region having the CDRs described in an amino acid sequence as set forth in any one of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128. In one embodiment, the invention provides an anti-CD137 antibody, or antigen-binding fragment thereof, comprising a light chain variable region having the CDRs described in an amino acid sequence as set forth in any one of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128; and a heavy chain variable region having the CDRs described in an amino acid sequence as set forth in any one of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 139, 140, 141, 142 and 143.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the present disclosure provides a fully human antibody of an IgG class that binds to a CD137 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, SEQ ID NO. 143, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof.

In one embodiment, the fully human antibody has both a heavy chain and a light chain wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A4 herein), SEQ ID NO. 5/SEQ ID NO. 6 (called A11 herein), SEQ ID NO. 7/SEQ ID NO. 8 (called B1 herein), SEQ ID NO. 9/SEQ ID NO. 10 (called B3 herein), SEQ ID NO. 11/SEQ ID NO. 12 (called B12 herein), SEQ ID NO. 13/SEQ ID NO. 14 (called C2 herein), SEQ ID NO. 15/SEQ ID NO. 16 (called C3 herein), SEQ ID NO. 17/SEQ ID NO. 18 (called C7 herein), SEQ ID NO. 19/SEQ ID NO. 20 (called C11 herein), SEQ ID NO. 21/SEQ ID NO. 22 (called C12 herein), SEQ ID NO. 23/SEQ ID NO. 24 (called D1 herein), SEQ ID NO. 25/SEQ ID NO. 26 (called D4 herein), SEQ ID NO. 27/SEQ ID NO. 28 (called D6 herein), SEQ ID NO. 29/SEQ ID NO. 30 (called D7 herein), SEQ ID NO. 31/SEQ ID NO. 32 (called D8 herein), SEQ ID NO. 33/SEQ ID NO. 34 (called D10 herein), SEQ ID NO. 35/SEQ ID NO. 36 (called E2 herein), SEQ ID NO. 37/SEQ ID NO. 38 (called E5 herein), SEQ ID NO. 39/SEQ ID NO. 40 (called E7 herein), SEQ ID NO. 41/SEQ ID NO. 42 (called F5 herein), SEQ ID NO. 43/SEQ ID NO. 44 (called F7 herein), SEQ ID NO. 45/SEQ ID NO. 46 (called F11 herein), SEQ ID NO. 47/SEQ ID NO. 48 (called G1 herein), SEQ ID NO. 49/SEQ ID NO. 50 (called G2 herein), SEQ ID NO. 51/SEQ ID NO. 52 (called G3 herein), SEQ ID NO. 53/SEQ ID NO. 54 (called G5 herein), SEQ ID NO. 55/SEQ ID NO. 56 (called G6 herein), SEQ ID NO. 57/SEQ ID NO. 58 (called G8 herein), SEQ ID NO. 59/SEQ ID NO. 60 (called G12 herein), SEQ ID NO. 61/SEQ ID NO. 62 (called H4 herein), SEQ ID NO. 63/SEQ ID NO. 64 (called H7 herein), SEQ ID NO. 65/SEQ ID NO. 66 (called H8 herein), SEQ ID NO. 67/SEQ ID NO. 68 (called H10 herein), SEQ ID NO. 69/SEQ ID NO. 70 (called H11 herein), SEQ ID NO. 71/SEQ ID NO. 72 (called C3sh1A1 herein), SEQ ID NO. 73/SEQ ID NO. 74 (called C3sh1A2 herein), SEQ ID NO. 75/SEQ ID NO. 76 (called C3sh1A5 herein), SEQ ID NO. 77/SEQ ID NO. 78 (called C3sh1A9 herein), SEQ ID NO. 79/SEQ ID NO. 80 (called C3sh1B2 herein), SEQ ID NO. 81/SEQ ID NO. 82 (called C3sh1B4 herein), SEQ ID NO. 83/SEQ ID NO. 84 (called C3sh1B6 herein), SEQ ID NO. 85/SEQ ID NO. 86 (called C3sh1B9 herein), SEQ ID NO. 87/SEQ ID NO. 88 (called C3sh1C1 herein), SEQ ID NO. 89/SEQ ID NO. 90 (called C3sh1C2 herein), SEQ ID NO. 91/SEQ ID NO. 92 (called C3sh1C7 herein), SEQ ID NO. 93/SEQ ID NO. 94 (called C3sh1D1 herein), SEQ ID NO. 95/SEQ ID NO. 96 (called C3sh1D4 herein), SEQ ID NO. 97/SEQ ID NO. 98 (called C3sh1D6 herein), SEQ ID NO. 99/SEQ ID NO. 100 (called C3sh1E2 herein), SEQ ID NO. 101/SEQ ID NO. 102 (called C3sh1E7 herein), SEQ ID NO. 103/SEQ ID NO. 104 (called C3sh1E9 herein), SEQ ID NO. 105/SEQ ID NO. 106 (called C3sh1F1 herein), SEQ ID NO. 107/SEQ ID NO. 108 (called C3sh1F10 herein), SEQ ID NO. 109/SEQ ID NO. 110 (called C3sh1F12 herein), SEQ ID NO. 111/SEQ ID NO. 112 (called C3sh1F2 herein), SEQ ID NO. 113/SEQ ID NO. 114 (called C3sh1G1 herein), SEQ ID NO. 115/SEQ ID NO. 116 (called C3sh1G11 herein), SEQ ID NO. 117/SEQ ID NO. 118 (called C3sh1G2 herein), SEQ ID NO. 119/SEQ ID NO. 120 (called C3sh1G3 herein), SEQ ID NO. 121/SEQ ID NO. 122 (called C3sh1G5 herein), SEQ ID NO. 123/SEQ ID NO. 124 (called C3sh1G8 herein), SEQ ID NO. 125/SEQ ID NO. 126 (called C3sh1H10 herein), SEQ ID NO. 127/SEQ ID NO. 128 (called C3sh1H4 herein), SEQ ID NO. 129/SEQ ID NO. 28 (called MA8 herein), SEQ ID NO. 130/SEQ ID NO. 28 (called MB1 herein), SEQ ID NO. 131/SEQ ID NO. 28 (called MB3 herein), SEQ ID NO. 132/SEQ ID NO. 28 (called MB10 herein), SEQ ID NO. 133/SEQ ID NO. 28 (called MB12 herein), SEQ ID NO. 134/SEQ ID NO. 28 (called MC8 herein), SEQ ID NO. 135/SEQ ID NO. 28 (called MD1 herein), SEQ ID NO. 136/SEQ ID NO. 28 (called MD4 herein), SEQ ID NO. 137/SEQ ID NO. 28 (called MSA11 herein), SEQ ID NO. 138/SEQ ID NO. 28 (called MSB7 herein), SEQ ID NO. 139/SEQ ID NO. 28 (called MSD2 herein), SEQ ID NO. 140/SEQ ID NO. 28 (called MSE3 herein), SEQ ID NO. 141/SEQ ID NO. 28 (called MSE5 herein), SEQ ID NO. 142/SEQ ID NO. 28 (called MSC8 herein), SEQ ID NO. 143/SEQ ID NO. 28 (called MSH1 herein), and combinations thereof.

In one embodiment, the invention provides an anti-CD137 antibody, or an antigen-binding fragment thereof, comprising a heavy chain comprising a CDR3 domain as set forth in any one of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 139, 140, 141, 142 and 143 and comprising a variable domain comprising an amino acid sequence that has at least 95%, at least 96%, at least 97%, at least 98%, or at least 99% identical to a sequence as set forth in any one of SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 130, 131, 132, 133, 134, 135, 136, 137, 139, 140, 141, 142 and 143. In one embodiment, the invention provides an anti-CD137 antibody, or an antigen-binding fragment thereof, comprising a light chain comprising a CDR3 domain as set forth in any one of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128 and having a light chain variable domain comprising an amino acid sequence that has at least 95%, at least 96%, at least 97%, at least 98%, or at least 99% identical to a sequence as set forth in any one of SEQ ID Nos: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126 and 128. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to CD137 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 5.

In one embodiment, the present invention is directed to an antibody, or an antigen binding fragment thereof, having antigen binding regions of antibody D6. In one embodiment, the invention provides an antibody, or antigen-binding fragment thereof, comprising a heavy chain variable domain sequence as set forth in SEQ ID NO: 27, and a light chain variable domain sequence as set forth in SEQ ID NO: 28. In one embodiment, the invention is directed to an antibody having a heavy chain variable domain comprising the CDRs of SEQ ID NO: 27, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 27, and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or an antigen binding fragment thereof, having antigen binding regions of antibody MB3. In one embodiment, the invention provides an antibody, or antigen-binding fragment thereof, comprising a heavy chain variable domain sequence as set forth in SEQ ID NO: 131, and a light chain variable domain sequence as set forth in SEQ ID NO: 28. In one embodiment, the invention is directed to an antibody having a heavy chain variable domain comprising the CDRs of SEQ ID NO: 131, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 131 and comprises a light chain variable region having an amino acid sequence that is at least 95% identical, at least 96% identical, at least 97% identical, at least 98% identical, or at least 99% identical to the sequence set forth in SEQ ID NO:28. The antibody may further be an IgG1 or an IgG4 isotype.

In one embodiment, the present invention is directed to an antibody, or an antigen binding fragment thereof, having antigen binding regions of antibody MSH1. In one embodiment, the invention provides an antibody, or antigen-binding fragment thereof, comprising a heavy chain variable domain sequence as set forth in SEQ ID NO: 143, and a light chain variable domain sequence as set forth in SEQ ID NO: 28. In one embodiment, the invention is directed to an antibody having a heavy chain variable domain comprising the CDRs of SEQ ID NO: 143, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 143 and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or an antigen binding fragment thereof, having antigen binding regions of antibody MB12. In one embodiment, the invention provides an antibody, or antigen-binding fragment thereof, comprising a heavy chain variable domain sequence as set forth in SEQ ID NO: 133, and a light chain variable domain sequence as set forth in SEQ ID NO: 28. In one embodiment, the invention is directed to an antibody having a heavy chain variable domain comprising the CDRs of SEQ ID NO: 133, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 133 and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or an antigen binding fragment thereof, having antigen binding regions of antibody MB10. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 28. In one embodiment, the invention is directed to an antibody having a heavy chain variable domain comprising the CDRs of SEQ ID NO: 132, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132 and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or an antigen binding fragment thereof, having antigen binding regions of antibody MB1. In one embodiment, the invention provides an antibody, or antigen-binding fragment thereof, comprising a heavy chain variable domain sequence as set forth in SEQ ID NO: 130, and a light chain variable domain sequence as set forth in SEQ ID NO: 28. In one embodiment, the invention is directed to an antibody having a heavy chain variable domain comprising the CDRs of SEQ ID NO: 130, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 130 and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or an antigen binding fragment thereof, having antigen binding regions of antibody MSC8. In one embodiment, the invention provides an antibody, or antigen-binding fragment thereof, comprising a heavy chain variable domain sequence as set forth in SEQ ID NO: 142, and a light chain variable domain sequence as set forth in SEQ ID NO: 28. In one embodiment, the invention is directed to an antibody having a heavy chain variable domain comprising the CDRs of SEQ ID NO: 142, and a light chain variable domain comprising the CDRs of SEQ ID NO:28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 142 and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an antibody, or an antigen binding fragment thereof, having antigen binding regions of antibody MSB7. In one embodiment, the invention provides an antibody, or antigen-binding fragment thereof, comprising a heavy chain variable domain sequence as set forth in SEQ ID NO: 138, and a light chain variable domain sequence as set forth in SEQ ID NO: 28. In one embodiment, the invention is directed to an antibody having a heavy chain variable domain comprising the CDRs of SEQ ID NO: 138, and a light chain variable domain comprising the CDRs of SEQ ID NO:28. The antibody may further be an IgG1 or an IgG4 isotype.

As described in Table 5, a number of heavy chain variable domain amino acid sequences are at least 95% identical to SEQ ID NO: 27. A number of heavy chain variable domains have amino acid sequences that are at least 95% identical to SEQ ID NO: 27, including SEQ ID NO: 143 (as described for antibody MSH1), SEQ ID NO: 142 (as described for antibody MSC8), SEQ ID NO: 130 (as described for antibody MB1), SEQ ID NO: 131 (as described for antibody MB3), SEQ ID NO: 132 (as described for antibody MB10), SEQ ID NO: 129 (as described for antibody MA8), SEQ ID NO: 133 (as described for antibody MB12) and SEQ ID NO: 135 (as described for antibody MD1).

A number of heavy chain variable domains have amino acid sequences that are at least 95% identical to SEQ ID NO: 141, including SEQ ID NO: 139 (as described for antibody MSD2), SEQ ID NO: 143 (as described for antibody MSH1), SEQ ID NO: 142 (as described for antibody MSC8) and SEQ ID NO: 129 (as described for antibody MA8).

A number of heavy chain variable domains have amino acid sequences that are at least 95% identical to SEQ ID NO: 139, including SEQ ID NO: 143 (as described for antibody MSH1) and SEQ ID NO: 142 (as described for antibody MSC8).).

A number of heavy chain variable domains have amino acid sequences that are at least 95% identical to SEQ ID NO: 143, including SEQ ID NO: 139 (as described for antibody MSD2), SEQ ID NO: 142 (as described for antibody MSC8), SEQ ID NO: 130 (as described for antibody MB1), SEQ ID NO: 27 (as described for antibody D6) and SEQ ID NO: 129 (as described for antibody MA8).

A number of heavy chain variable domains have amino acid sequences that are at least 95% identical to SEQ ID NO: 142, including SEQ ID NO: 141 (as described for antibody MSE5), SEQ ID NO: 139 (as described for antibody MSD2), SEQ ID NO: 142 (as described for antibody MSC8), SEQ ID NO: 143 (as described for antibody MSH1), SEQ ID NO: 130 (as described for antibody MB1), SEQ ID NO: 131 (as described for antibody MB3), SEQ ID NO: 132 (as described for antibody MB10), SEQ ID NO: 27 (as described for antibody D6), SEQ ID NO: 133 (as described for antibody MB12) and SEQ ID NO: 135 (as described for antibody MD1).

A number of heavy chain variable domains have amino acid sequences that are at least 95% identical to SEQ ID NO: 130, including SEQ ID NO: 143 (as described for antibody MSH1), SEQ ID NO: 142 (as described for antibody MSC8), SEQ ID NO: 131 (as described for antibody MB3), SEQ ID NO: 132 (as described for antibody MB10), SEQ ID NO: 27 (as described for antibody D6), SEQ ID NO: 133 (as described for antibody MB12) and SEQ ID NO: 135 (as described for antibody MD1).

A number of heavy chain variable domains have amino acid sequences that are at least 95% identical to SEQ ID NO: 131, including SEQ ID NO: 142 (as described for antibody MSC8), SEQ ID NO: 130 (as described for antibody MB1), SEQ ID NO: 132 (as described for antibody MB10), SEQ ID NO: 27 (as described for antibody D6), SEQ ID NO: 133 (as described for antibody MB12) and SEQ ID NO: 135 (as described for antibody MD1).

A number of heavy chain variable domains have amino acid sequences that are at least 95% identical to SEQ ID NO: 132, including SEQ ID NO: 142 (as described for antibody MSC8), SEQ ID NO: 130 (as described for antibody MB1), SEQ ID NO: 131 (as described for antibody MB3), SEQ ID NO: 132 (as described for antibody MB10), SEQ ID NO: 27 (as described for antibody D6), SEQ ID NO: 133 (as described for antibody MB12) and SEQ ID NO: 135 (as described for antibody MD1).

A number of heavy chain variable domains have amino acid sequences that are at least 95% identical to SEQ ID NO: 129, including SEQ ID NO: 143 (as described for antibody MSH1), SEQ ID NO: 130 (as described for antibody MB1), SEQ ID NO: 131 (as described for antibody MB3), SEQ ID NO: 132 (as described for antibody MB10), SEQ ID NO: 27 (as described for antibody D6), SEQ ID NO: 133 (as described for antibody MB12) and SEQ ID NO: 135 (as described for antibody MD1).

A number of heavy chain variable domains have amino acid sequences that are at least 95% identical to SEQ ID NO: 133, including SEQ ID NO: 142 (as described for antibody MSC8), SEQ ID NO: 130 (as described for antibody MB1), SEQ ID NO: 131 (as described for antibody MB3), SEQ ID NO: 132 (as described for antibody MB10), SEQ ID NO: 27 (as described for antibody D6), SEQ ID NO: 129 (as described for antibody MA8) and SEQ ID NO: 135 (as described for antibody MD1).

A number of heavy chain variable domains have amino acid sequences that are at least 95% identical to SEQ ID NO: 135, including SEQ ID NO: 142 (as described for antibody MSC8), SEQ ID NO: 130 (as described for antibody MB1), SEQ ID NO: 131 (as described for antibody MB3), SEQ ID NO: 132 (as described for antibody MB10), SEQ ID NO: 27 (as described for antibody D6) and SEQ ID NO: 133 (as described for antibody MB12).

SEQ ID NO 28 is included as the light chain variable domain in a number of antibodies, including D6, MA8, MB1, MB3, MB10, MB12, MC8, MD1, MD4, MSA11, MSB7, MSD2, MSE3, MSE5, MSC8 and MSH1, as described in Table 5. A number of light chain variable domains have amino acid sequences that are at least 95% identical to SEQ ID NO:28, including SEQ ID NO: 62 (as described for antibody H4), SEQ ID NO: 90 (as described for antibody C3sh1C2) and SEQ ID NO: 84 (as described for antibody C3sh1B6).

A number of light chain variable domains have amino acid sequences that are at least 95% identical to SEQ ID NO: 22, including SEQ ID NO: 118 (as described for antibody C3sh1G2) and SEQ ID NO: 14 (as described for antibody C2).

A number of light chain variable domains have amino acid sequences that are at least 95% identical to SEQ ID NO: 128, including SEQ ID NO: 50 (as described for antibody G2) and SEQ ID NO: 126 (as described for antibody C3sh1H10).

A number of light chain variable domains have amino acid sequences that are at least 95% identical to SEQ ID NO: 126, including SEQ ID NO: 50 (as described for antibody G2), SEQ ID NO: 128 (as described for antibody C3sh1H4), SEQ ID NO: 40 (as described for antibody E7), and SEQ ID NO: 98 (as described for antibody C3sh1D6).

Antigen binding proteins (e.g., antibodies, antibody fragments, antibody derivatives, antibody muteins, and antibody variants) are polypeptides that bind to CD137.

Antigen-binding fragments of antigen binding proteins of the invention may be produced by conventional techniques. Examples of such fragments include, but are not limited to, Fab and F(ab')2 fragments.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, SEQ ID NO. 143, and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 139/SEQ ID NO. 28, SEQ ID NO. 140/SEQ ID NO. 28, SEQ ID NO. 141/SEQ ID NO. 28, SEQ ID NO. 142/SEQ ID NO. 28, SEQ ID NO. 143/SEQ ID NO. 28, and combinations thereof.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, SEQ ID NO. 143, and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 139/SEQ ID NO. 28, SEQ ID NO. 140/SEQ ID NO. 28, SEQ ID NO. 141/SEQ ID NO. 28, SEQ ID NO. 142/SEQ ID NO. 28, SEQ ID NO. 143/SEQ ID NO. 28, and combinations thereof.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSC→CPPC) in the hinge region (Bloom et al., 1997, *Protein Science* 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2). Thus, the invention also includes, in certain embodiments, variable sequences having at least 95% identity, at least 96% identity, at least 97% identity, at least 98% identity, or at least 99% identity to those sequences disclosed herein.

In certain embodiments, an antibody, or antigen-binding fragment thereof, provided herein has a dissociation constant ($K_d$) of $1 \times 10^{-6}$ M or less; $5 \times 10^{-7}$ M or less' $1 \times 10^{-7}$ M or less; $5 \times 10^{-8}$ M or less; $1 \times 10^{-8}$ M or less; $5 \times 10^{-9}$ M or less; or $1 \times 10$ M or less. In one embodiment, the antibody, or antigen-binding fragment thereof, of the invention as a Kd from $1 \times 10^{-7}$ M to $1 \times 10^{-10}$ M. In one embodiment, the antibody, or antigen-binding fragment thereof, of the invention as a $K_d$ from $1 \times 10^{-8}$ M to $1 \times 10^{-10}$ M.

Those of ordinary skill in the art will appreciate standard methods known for determining the Kd of an antibody, or fragment thereof. For example, in one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)).

According to another embodiment, Kd is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

In particular embodiments, antigen binding proteins of the present invention have a binding affinity ($K_a$) for CD137 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from CD137. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to CD137 with substantially the same $K_{off}$ as an antibody described herein.

In another aspect, the present disclosure provides an antigen binding protein that binds to CD137 expressed on the surface of a cell and, when so bound, inhibits CD137 signaling activity in the cell without causing a significant reduction in the amount of CD137 on the surface of the cell. Any method for determining or estimating the amount of CD137 on the surface and/or in the interior of the cell can be used. In other embodiments, binding of the antigen binding protein to the CD137-expressing cell causes less than about 75%, 50%, 40%, 30%, 20%, 15%, 10%, 5%, 1%, or 0.1% of the cell-surface CD137 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of CD137, or to an epitope of CD137 and an epitope of another molecule, via two different antigen binding sites or regions. Moreover, bispecific antigen binding protein as disclosed herein can comprise a CD137 binding site from one of the herein-described antibodies and a second CD137 binding region from another of the herein-described antibodies, including those described herein by reference to other publications. Alternatively, a bispecific antigen binding protein may comprise an antigen binding site from one of the herein described antibodies and a second antigen binding site from another CD137 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, Nature 305:537, and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Oligomers that contain one or more antigen binding proteins may be employed as CD137 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CD137 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a CD137 binding fragment of an anti-CD137 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-CD137 antibody fragment or derivative fused to a leucine zipper peptide are expressed in suitable host cells, and the soluble oligomeric anti-CD137 antibody fragments or derivatives that form are recovered from the culture supernatant.

Antigen binding proteins directed against CD137 can be used, for example, in assays to detect the presence of CD137 polypeptides, either in vitro or in vivo. The antigen binding proteins also may be employed in purifying CD137 proteins by immunoaffinity chromatography. Such antigen binding proteins that function as CD137 agonists may be employed in treating any CD137-induced condition, including but not limited to various cancers.

Antigen binding proteins may be employed in an in vitro procedure, or administered in vivo to enhance CD137-induced biological activity. Disorders that would benefit (directly or indirectly) from activation of CD137, examples of which are provided herein, thus may be treated. In one embodiment, the present invention provides a therapeutic method comprising in vivo administration of a CD137 activating antigen binding protein to a mammal in need thereof in an amount effective for increasing a CD137-induced biological activity.

In certain embodiments of the invention, antigen binding proteins include fully human monoclonal antibodies that enhance a biological activity of CD137.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CD137 bound thereto. Polypeptides contemplated for use herein include substantially homogeneous recombinant mammalian anti-CD137 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CD137 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual, Vols.* 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

CD137-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to CD137. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag4 1, Sp210-Ag14, FO, NSO/U, MPC-11, MPC11-X45-GTG 1.7 and S194/5XX0 Bul; examples of cell lines used in rat fusions include R210.RCY3, Y3-Ag1.2.3, IR983F and 48210. Other cell lines useful for cell fusions are U-266, GM1500-GRG2, LICR-LON-HMy2 and UC729-6.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Methods, Formulations and Modes of Administration

The present disclosure further provides a method for treating a disease requiting either stimulation of immune responses, comprising administering an anti-CD137 polypeptide. Any of the antibodies disclosed herein may be used in such methods. For example, the methods may be performed using an anti-CD137 polypeptide selected from the group consisting of a fully human antibody of an IgG class that binds to a CD137 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, including the heavy and light chain variable regions (and CDRs within said sequences) described in SEQ ID Nos. 1-143 (Table 5).

For example, in one embodiment, the methods disclosed herein include the use of a fully human antibody having a heavy chain variable domain sequence that is at least 95% identical, at least 96% identical, at least 97% identical, at least 98% identical, or at least 99% identical, to an amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, and SEQ ID NO. 143, and that having a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128.

In one embodiment, the methods described herein include the use of a fully human Fab antibody fragment has the heavy chain variable domain sequence that is at least 95% identical, at least 96% identical, at least 97% identical, at least 98% identical, or at least 99% identical, to an amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, and SEQ ID NO. 143, and that has the light chain variable domain sequence that is at least 95% identical, at least 96% identical, at least 97% identical, at least 98% identical, or at least 99% identical, to the amino acid sequence consisting SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128.

In one embodiment, the methods described herein include the use of a single chain human antibody having a heavy chain variable domain sequence that is at least 95% identical, at least 96% identical, at least 97% identical, at least 98% identical, or at least 99% identical to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 130, SEQ ID NO. 131, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO. 142, and SEQ ID NO. 143, and having a light chain variable domain sequence that is at least 95% identical, at least 96% identical, at least 97% identical, at least 98% identical, or at least 99% identical, to an amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, and SEQ ID NO. 128.

In one embodiment, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 139/SEQ ID NO. 28, SEQ ID NO. 140/SEQ ID NO. 28, SEQ ID NO. 141/SEQ ID NO. 28, SEQ ID NO. 142/SEQ ID NO. 28, and SEQ ID NO. 143/SEQ ID NO. 28.

In one embodiment, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 139/SEQ ID NO. 28, SEQ ID NO. 140/SEQ ID NO. 28, SEQ ID NO. 141/SEQ ID NO. 28, SEQ ID NO. 142/SEQ ID NO. 28, and SEQ ID NO. 143/SEQ ID NO. 28.

In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 28, SEQ ID NO. 130/SEQ ID NO. 28, SEQ ID NO. 131/SEQ ID NO. 28, SEQ ID NO. 132/SEQ ID NO. 28, SEQ ID NO. 133/SEQ ID NO. 28, SEQ ID NO. 134/SEQ ID NO. 28, SEQ ID NO. 135/SEQ ID NO. 28, SEQ ID NO. 136/SEQ ID NO. 28, SEQ ID NO. 137/SEQ ID NO. 28, SEQ ID NO. 138/SEQ ID NO. 28, SEQ ID NO. 28, SEQ ID NO. 139/SEQ ID NO. 28, SEQ ID NO.

140/SEQ ID NO. 28, SEQ ID NO. 141/SEQ ID NO. 28, SEQ ID NO. 142/SEQ ID NO. 28, and SEQ ID NO. 143/SEQ ID NO. 28.

In one embodiment, the anti-CD137 antibodies and antibody fragments of the invention are used to treat a disease is selected from the group consisting of cancers, autoimmune diseases and viral infections.

Due to the role of CD137 signaling in promoting T cell and NK cell proliferation, IFN-γ secretion, and prolonging the survival of CD8+ T cells, CD137 engagement may provide an attractive strategy for immunotherapy of cancer. Antibodies against CD137 have variable anti-tumor therapeutic effects depending on the immunogenicity of the experimental tumor and anatomical site of tumor growth. Treatment with agonist anti-CD137 mAbs caused regression of large, well-established tumors in mice, including Ag104A sarcoma, P815 mastocytoma, EL4E7 lymphomas and B10.2 fibrosarcoma. This treatment also generated systemic anti-tumor effects in established intracranial tumors including MCA sarcoma and GL261 glioma, but not in established subcutaneous and pulmonary tumors.

Altogether, CD137 stimulation results in enhanced expansion, survival, and effector functions of newly primed CD8+ T-cells, acting, in part, directly on these cells. Both CD4+ and CD8+ T-cells have been shown to respond to CD137 stimulation, however, it appears that enhancement of T-cell function is greater in CD8+ cells (W. Shuford et al., J. Exp. Med., 186(1):47-55 (1997); I. Gramaglia et al., Eur. J. Immunol., 30(2):392-402 (2000); C. Takahashi et al., J. Immunol., 162:5037 (1999)). Based on the critical role of CD137 stimulation in CD8+ T-cell function and survival, manipulation of the CD137/CD137L system provides an approach for the treatment of tumors and viral pathogens. Thus, in one embodiment, the anti-CD137 agonist antibodies of the invention (e.g., those described in Table 5) may be used in a method of treating a patient having a cancer, including, for example, ovarian cancer, colorectal cancer (e.g. colorectal adenocarcinoma), melanoma, hepatocellular carcinoma, renal cancer, breast cancer, head and neck cancer, lung cancer, non-hodgkin lymphoma, and liver cancer.

CD137 seems to play a role in CD8+ T cell-mediated antiviral responses. CD137L-deficient mice had decreased CTL responses to influenza virus in the late stage of primary response and defective secondary response. There was also diminished CD8+ T cell responses and IFN-γ expression after lymphocytic choriomeningitis virus (LCMV) infection. There was impaired efficacy of vaccination with LCMV peptide in long term protection generation against LCMV infection. CD137-deficient mice showed decreased CTL activity against vesicular stomatitis virus (VSV). However, these mice showed normal humoral immune responses to viruses.

CD137 stimulation also restored CD8+ T cell response to an immunodominant influenza epitope in the absence of CD28 stimulation. Promoting CD8+ T cell responses by modifying CD137 signaling may be a useful approach to improve antiviral CD8+ T cell responses.

CD137/CD137L interaction plays an important role in regulating alloresponses in vivo. Anti-CD137 mAbs enhance cardiac allograft and MHC-mismatched skin transplant rejection with dramatically increased INF-γ production by CD8+ T cells and CTL activity against alloantigens. Blocking CD137/CD137L interaction by anti-CD137L mAbs significantly inhibited rejection of intestinal allografts by CD8+ but not CD4+ T cells. Anti-CD137 mAbs promoted both CD8+ and CD4+ T cell-mediated graft-versus-host disease (GVHD) and host anti-donor-mediated graft rejection could be regulated through CD137/CD137L interaction by using anti-CD137 mAbs, CD137−/− donor T cells, or CD137L−/− recipients. Blocking CD137/CD137L interaction may reduce GVHD and prevent CD8+ T cell-mediated allograft rejection. For allograft rejection involving both CD4+ and CD8+ T cells, combined blockade of CD137/CD137L and other costimulatory signaling is required.

T cells are involved in the pathogenesis of many autoimmune diseases. The activation of T cells in response to their cognate peptide/MHC targets requires costimulatory signals delivered by APCs occurring at multiple steps. Conventional costimulation blockade is an attractive therapeutic approach for the treatment of T cell-dependent auto immune diseases. Anti-CD137 Mabs can block several costimulatory pathways, such as CD28/B7, CD40L/CD40 and OX-40L/OX-40R, with either soluble receptors or neutralizing anti-ligand mAbs. However, costimulatory agonists of CD137 could also prevent and have therapeutic effects on CD4+ T cell-involved autoimmune diseases. A single low dose of agonistic anti-CD137 mAb treatment prevented the development of EAE, a Th1 cell-mediated demyelinating disease of the central nervous system used as a murine model for human multiple sclerosis. Draining lymph node cells from anti-4-1BB-treated mice failed to respond to antigen stimulation in vitro or to transfer disease to RAG-1-deficient recipient mice. When treatment was initiated after disease onset, early EAE relapse was also inhibited. Agonistic anti-4-1BB mAbs treatment initially increased T cell activation, and then promoted the clearance of these activated CD4+ T cells, resulting in the attenuation of their effector functions. Administering agonistic anti-CD137 mAbs also showed promising therapeutic effect in both CD4+ T cell and B cell involved spontaneous systemic autoimmune disease. MRL/lpr mice spontaneously develop lymphadenopathy and a severe autoimmune disease resembling human SLE due to the lymphoproliferative (lpr) mutation in the Fas gene. Short-term treatment with anti-CD137 blocked lymphadenopathy and spontaneous autoimmune diseases in MRL/lpr mice, ultimately leading to their prolonged survival. This therapeutic regimen was also effective when started after the mice had already showed clinically detectable autoimmune disease. The therapeutic effects of anti-CD137 were mediated by the depletion of auto-reactive B cells, activated CD4+ T cells and the aberrant CD4-CD8-B220+CD3+ T cells that principally contribute to lymphadenopathy in MRL/lpr mice. Giving lupus-prone NZB× NZW F1 female mice three injections of anti-CD137 mAbs between 26 and 35 weeks of age reversed acute disease, blocked chronic disease, and prolonged the mice's lifespan. Autoantibody production in treated mice, regardless of their age or disease status, was rapidly suppressed without inducing systemic immunosuppression or massive depletion of lymphocytes. In this model, adoptive transfer of antigen-primed CD4+ T cells or DCs overrode anti-CD137-mediated protection, which suggests that unresponsiveness is not achieved by active suppression. However, CD137 engagement in vivo does not ameliorate all autoimmune diseases. Transgenic non-obese diabetic (NOD) mice overexpressing membrane-bound agonistic anti-CD137 scFv in pancreatic beta cells exhibited increased GAD-specific T cell responses, and developed more severe diabetes than their non-transgenic littermates, with earlier onset, faster diabetic processes, and higher mortality. Anti-CD137 treatment, starting around the onset of disease, promoted disease onset in NOD mice. Thus, in one embodiment, the anti-CD137 agonist antibodies of the invention (e.g., those described in Table 5) may be used in a method of treating a patient having an autoimmune disease, including, for example, multiple sclerosis, rheumatoid arthritis, systemic lupus erythematosus, and myaesthenia gravis.

The present disclosure features methods for treating or preventing the *S. aureus* infection comprising administering an anti-CD137 polypeptide. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

In certain embodiments, the disclosed antibodies are administered by inhalation, but aerosolization of full IgG antibodies may prove limiting due to their molecular size (~150 kDa). To maximize available commercial aerosolization devices, smaller Fab fragments may be required. In this case, we may also need to generate Fab fragments from the parental IgG molecules. Therefore, we will perform initial studies using standard enzyme-based digestion methodologies for the generation of Fab fragments, which will then be characterized in parallel with full IgG molecules.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 μg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

A CD137 binding polypeptide, as disclosed herein, can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-CD137 antibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to CD137. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CD137 protein is combined with the subject binding polypeptides, binding occurs between the binding polypeptides and the CD137 protein. In one embodiment, a sample containing cells expressing a CD137 protein (e.g., endothelial cells) is combined with the subject antibodies, and binding occurs between the binding polypeptides and cells bearing a CD137 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CD137 protein in a biological sample can also be prepared. Such kits will include a CD137 binding polypeptide which binds to a CD137 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

Having now described the present invention in detail, the same will be more clearly understood by reference to the following examples, which are included for purposes of illustration only and are not intended to be limiting of the invention.

Example 1

Human antibodies specific for human CD137 were identified and selected for therapeutic characteristics, including specificity for CD137 and a high degree of affinity for CD137 (e.g., at least $10^{-6}$ M). The identified antibodies are described in Table 5.

To demonstrate agonistic activity, the ability of the anti-CD137 antibodies (specifically D6, C3sh1G3, C7, and C3sh1F10) to mediate costimulatory activity was assessed. Both anti-CD137 antibodies and anti-CD3 antibody were added to the wells of a 96 well plate in PBS to immobilize the antibodies to the plate. The anti-CD137 was at 10 microgram/ml and the anti-CD3 was at 3 microgram/ml. After a minimum of 2 hours at room temperature, the wells were washed and monocyte depleted lymphocytes were added to the wells at $2 \times 10^5$ per well. The monocytes were depleted by labeling peripheral blood mononuclear cells (PBMC) with biotinylated anti-CD14 antibody followed by incubation with anti-biotin magnetic beads. Passage over a column in the presence of a magnet resulted in depletion of the monocytes.

Figure 1B:
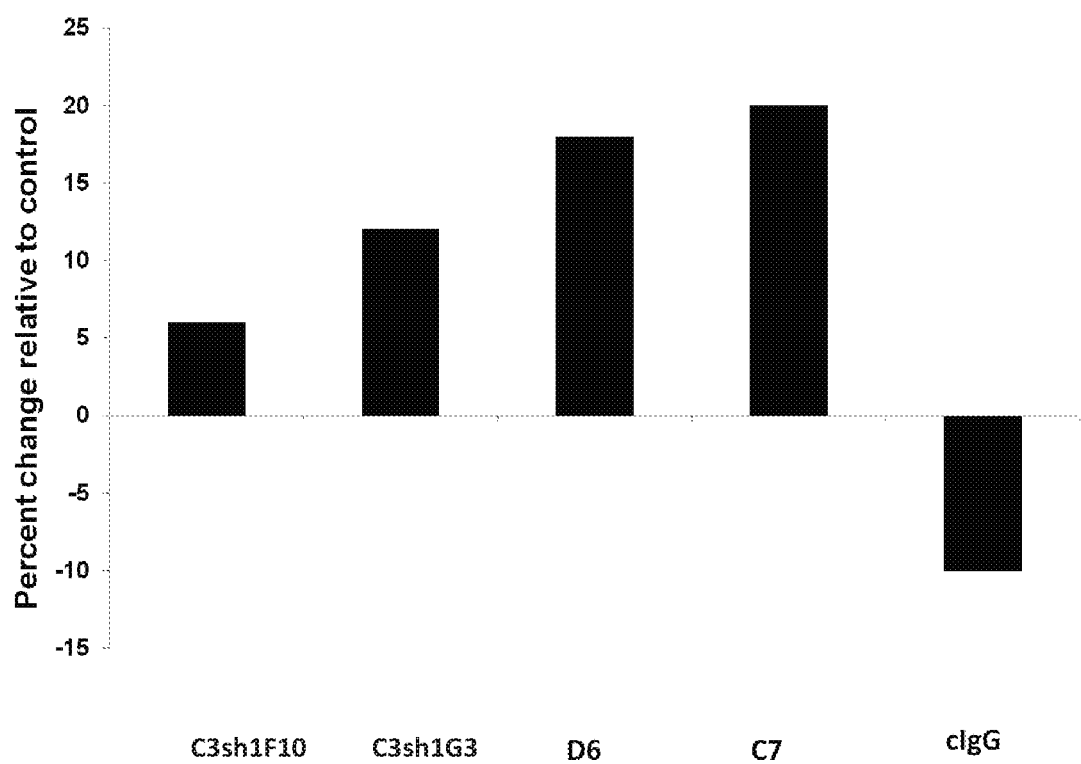
FIG. 1B is a graph that shows the results of FIG. 1A, normalized relative to the cultures receiving no antibody. A notable level of augmentation was detected in cultures which received the tested anti-CD137 antibodies, and in particular the D6 and C7 antibodies.

To measure cell activation, the cells were labeled with FITC anti-human CD25 after three days of culture. The percentage of cells positive for CD25 expression was measured by flow cytometry and is described in FIG. 1A. The percent change from normal, or normalized data, was determined by the below formula and the results are shown in FIG. 1B.

$$\left( \frac{\text{test \% } CD25 - \text{control \% } CD25}{\text{control \% } CD25} \right) \times 100$$

The use of immobilized anti-CD137 antibodies in the assay facilitated their ability to mimic the ligand and promote signaling to the cell resulting in co-stimulation. From the data shown in FIG. 1A, antibody D6 consistently, in particular, provided a co-stimulatory signal to the T cells and is an agonistic anti-CD137 antibody. This is more apparent when the data are normalized relative to the control as shown in FIG. 1B.

Figure 3B:
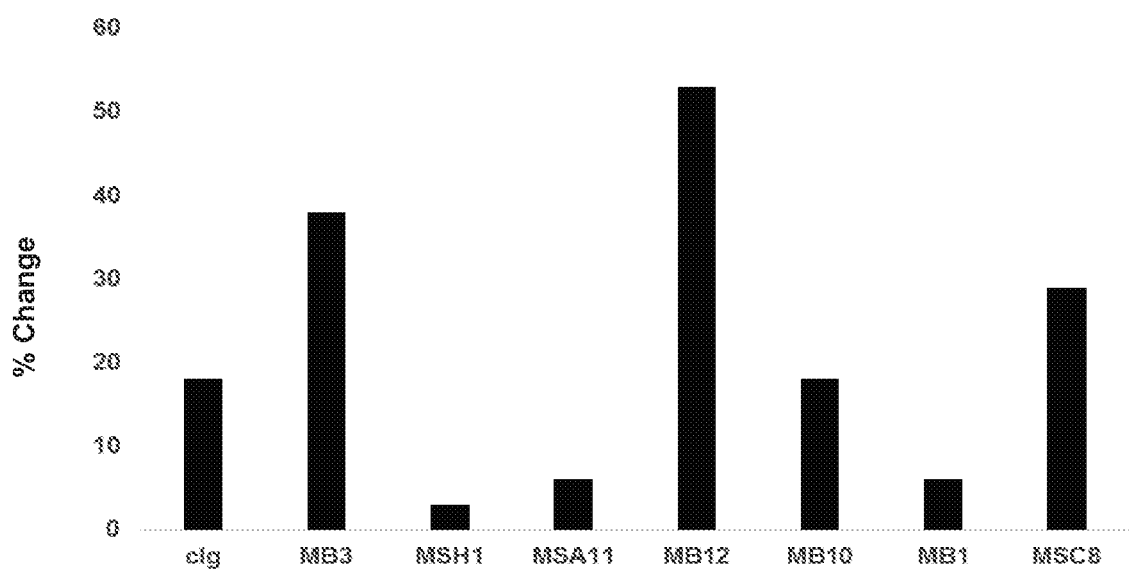

The above experiment was repeated in a third experiment testing anti-CD137 antibody D6 and D6 variants MA8, MB3, MSD2, MSH1, MSB7, MSA11, MD4, MB12, MB10, MB1, MSE5, MSC8, MSE3, MD1, and MC8 for their ability to increase CD25 activity as a measure of cell activation. The experiment was performed as described above, and the results are provided in FIGS. 3A and 3B (normalized; for certain antibodies). As shown in FIGS. 3A and 4B, out of many CD137 reactive antibodies tested, certain particular antibodies were identified that demonstrate agonistic activity.

Example 2

This example describes affinity characteristics for a number of anti-CD137 antibodies that were identified and are described in Table 5. Table 1 describes the affinity characteristics of antibodies MC8 and MSA11. Table 2 describes the affinity characteristics of antibodies MSB7, MSH1, and MD4. Table 3 describes the affinity characteristics of antibodies D6, MB3, and MSC8. Table 4 describes the binding characteristics of antibody B12.

Antibodies MC8, MSA1, MSB7, MSH1, MD4, D6, MB3, MSC8, and MB12 are variants of the D6 antibody. Each antibody has a light chain variable region comprising SEQ ID NO: 28, while the heavy chain of each is varied relative to D6.

TABLE 1

Binding characteristics of antibodies MC8 and MSA11

| name | ka (1/Ms) | kd (1/s) | Rmax (RU) | KA (1/M) | KD (M) | Chi2 |
|---|---|---|---|---|---|---|
| MC8 | 2.08E5 | 6.28E-3 | 296 | 3.32E7 | 3.02E-8 | 0.807 |
| MSA11 | 1.35E5 | 6.31E-3 | 293 | 2.13E7 | 4.69E-8 | 0.438 |

TABLE 2

Binding characteristics of antibodies MSB7, MSH1, and MD4

| name | ka (1/Ms) | kd (1/s) | Rmax (RU) | KA (1/M) | KD (M) | Chi2 |
|---|---|---|---|---|---|---|
| MSB7 | 4.56E5 | 7.56E-3 | 214 | 6.03E7 | 1.66E-8 | 1.66 |
| MSH1 | 3.69E5 | 0.0324 | 60.6 | 1.14E7 | 8.78E-8 | 0.675 |
| MD4 | 5.76E5 | 0.0512 | 71.3 | 1.12E7 | 8.89E-8 | 1.27 |

TABLE 3

Binding characteristics of antibodies D6, MB3, and MSC8

| Name | Ka (1/Ms) | Kd (1/s) | Rmax (RU) | KD (M) | Chi2 |
|---|---|---|---|---|---|
| D6 | 4.013E5 | 0.08137 | 64.5 | 2.028E-7 | 0.411 |
| MB3 | 2.959E5 | 0.0678 | 86.15 | 2.292E-7 | 1.87 |
| MSC8 | 2.816E5 | 0.0615 | 86.41 | 2.184E-7 | 1.51 |

TABLE 4

Binding characteristics of MB12 for CD137

| name | ka (1/Ms) | kd (1/s) | Rmax (RU) | KA (1/M) | KD (M) | Chi2 |
|---|---|---|---|---|---|---|
| MB12 | 4.33E5 | 0.0669 | 32.3 | 6.47E6 | 1.55E-7 | 0.0887 |

This example illustrates binding affinities of exemplary anti-CD137 antibodies disclosed herein. Affinities were determined using surface plasmon resonance (Biacore). Briefly, anti-human Fc antibody (GE, BR-1008-39) was immobilized on CM5 sensor chip to approximately 1000 RU using standard NHS/EDC coupling methodology. Antibodies (about 10 μg/ml) were captured for 60 s at a flow rate 10 μL/min. Recombinant human CD137/His was serially diluted in running buffer (HBS-EP). All measurements were conducted with a flow rate of 30 μL/min. Surfaces were regenerated with 3M $MgCl_2$ for 60 s. A 1:1 (Langmuir) binding model was used to fit the data.

Example 3

The following example describes the characterization of anti-CD137 antibodies D6, MB3, MSC8, and MB12. The amino acid sequence of the variable heavy and light chains of each of these antibodies is provided in Table 5.

Cross-reactivity studies of anti-CD137 antibodies D6, MB3, MSC8, and MB12 revealed that these antibodies are specific to human CD137 and to not cross react with murine CD137. Results from the cross-reactivity study are described in FIG. 2 and show that each antibody was specific for human CD137, and not murine CD137.

A Maxisorp plate was coated with recombinant human CD137/Fc or mouse CD137/Fc at 2 μg/mL at 4° C., overnight. The plate was blocked for 1 hour at room temperature, washed 3 times with PBS-Tween (PBST), then anti-CD137 antibodies (~1 μg/mL) diluted in casein were added and incubated for 30 min with shaking. The plate was washed 3 times with PBST, horseradish peroxidase (HRP)-conjugated mouse anti-human Lambda (1:1000 in casein) was added, then 3,3',5,5'-Tetramethylbenzidine (TMB) was added as substrate and developed about 5 min. 2M $H_2SO_4$ was used to stop the reaction and the OD was read at 450 nm.

TABLE 5

Heavy and Light Chain Variable Domain Amino Acid Sequences

| | Heavy chain variable domain regions | Light chain variable domain regions |
|---|---|---|
| A1 | EVQLVESGAEVKKPGASVKVSCKAS GYTFTSYYMHWVRQAPGQGLEWMG IINPSGGSTSYAQKFQGRVTMTRDTST STVYMELSSLRSEDTAVYYCAVPTDG YNYFGAFDIWGQGTMVTVSS SEQ ID NO. 1 | QAGLTQPPSVSEAPRQRVTISCSGSYS NIGFNAVSWYQQFPGEAPKLLIYYDD LLSSGVSGRFSGSRSGTSASLAISGLQS DDEAVYYCATWDDSVNGWVFGGGT KLTVL SEQ ID NO. 2 |
| A4 | EVQLVQSGGDLVRPGGSLRLSCTVSG LPYSDYYMHWIRQAPGKKLEWISDIG PRGTSVHYADSVKGRFTVSRDNTKNS LYLQMNNLRADDTAVYYCANAFSSS WFYNWGRGTLVTVSS SEQ ID NO. 3 | SSELTQDPAVSVALGQTVRITCQGDSL RRYYASWYQQKPGQAPILLIYGKDLR PSGIPDRFSGSSSENTASLTVTGAQAE DEGEYYCNSRDSSGNWVFGGGTQLT VL SEQ ID NO. 4 |
| A11 | QVQLVQSGAEVKKPGASVKVSCKAS GYTFTSYDINWVRQAPGQGLEWMG WIGTYNGVTNYAQTFQGRVSMTTDT STSTAYMELRSLRSDDTAVYYCARDA GPLDYWGQGTLVTVSS SEQ ID NO. 5 | EIVLTQSPSSLSASVGDRVTITCRASQS ISSYLNWYQQKPGKAPNLLIYGAS QSGVPSRFSGSGSGTDFTLTISSLQPED FATYYCQQSYTTPYTFGQGTKVDIK SEQ ID NO. 6 |
| B1 | EVQLLESGGGLVKPGGSLRLSCAASG FIFSTYAMTWVRQAPGKGLEWVSSIS SSSSYIYYADSVKGRFTISRDNAKNSL YLQMNSLRAEDTAVYYCARDEGVFD YWGQGTLVTVSS SEQ ID NO. 7 | QSVLTQPPSASGSPGQSVTISCTGTSSD VGAYNYVSWYQEYPGKAPKLMIYEV NKRPSGVPDRFSGSKSGNTASLTVSG LQAEDEADYYCSSYAGHNNPYVFGT GTKVTVL SEQ ID NO. 8 |

TABLE 5-continued

Heavy and Light Chain Variable Domain Amino Acid Sequences

| | Heavy chain variable domain regions | Light chain variable domain regions |
|---|---|---|
| B3 | QVQLVQSGAEVKKPGASVKVSCKTS GYTFTSYNMHWVRQAPGQGLEWMG VINPSDRYTWYAQKFRGRVTMTRDT STSTVYMELSSLRSEDTAIYYCARGGE DTASYYWGQGTLVTVSS SEQ ID NO. 9 | SSELTQDPAVSVALGQTLRITCQGDSL RSYYASWYQQKPGQAPVLVIYGKNN RPSGIPDRFSGSTSGNTDSLTITGAQAE DEADYFCSSRDSSD NHLNVLFGGGTK LTVL SEQ ID NO. 10 |
| B12 | QVQLVQSGGGLIQPGGSLRLSCAASG FTVSNNYMRWVRQAPGKGLEWVSLI YSTGTTYYADSVKGRFTISRDNSKNT LYLQMNSLRAEDTAVYYCARDRGQ WFDPWGQGTLVTVSS SEQ ID NO. 11 | SSELTQDPAVSVALGQTVRITCQGDSL RSYYASWYQQKPGQAPVLVIYGKNN RPSGIPDRFSGSSSGNTASLTITGAQAE DEADYYCHSRDSNGNHVIFGGGTKLT VL SEQ ID NO. 12 |
| C2 | EVQLVQSGAEVKKPGSSVKVSCKASG GTFSSYAISWVRQAPGQGLEWMGDIV PIFGVANYAQKFQGRVTMTRDTSTST VYMDLSSLRSEDTAVYYCARDRGAF DIWGQGTMVTVSS SEQ ID NO. 13 | AIRMTQSPSSLSASVGDRVTITCRASQ TISSYLNWYQQKPGKAPKLLIYGASSL QSGVPSRFSGSGSGTDFTLTISSLQPED FATYYCQQSYSTPWTFGQGKVDIK SEQ ID NO. 14 |
| C3 | QVQLVQSGAEVKKPGSSVKVSCKAS GGTFSSYAISWVRQAPGQGLEWMGGI IPIFGTANYAQKFQGRVTITADESTST AYMELSSLRSEDTAVYYCARVGRLER PYYFDYWGQGTLVTVSS SEQ ID NO. 15 | SYELTQPPSLSVAPGKTARITCGGDNI RSKSVNWYQQKPGQAPLLVISFDSDR PSGIPERVSGSNSGNTATLTISTVEAG DEADYYCQVWDGYVGVFGGGTQLT VL SEQ ID NO. 16 |
| C7 | QVQLVQSGTEVKKPGASVKVSCKAS GYTFTGYYIHWVRQAPGQGLEWMG WINPNSGGTNYAQKFQGRVTMTRDT SISTAYMELSRLRSDDTAVYYCARDY YDSSGYFGPDYWGQGTLVTVSS SEQ ID NO. 17 | QSALTQPPSASGSPGQSVTISCTGTSSD VGAYNFVSWYQQHPGKAPKLMIYDV SNRPSGVSNRFSGSKSGNTASLTISGL QAEDEADYYCSSYTSSSTRWVFGTGT KVTVL SEQ ID NO. 18 |
| C11 | EVQLVESGGALVQPGGSLRLSCAASG FTFTNFWMDWVRQAPGKGLEWVADI NKDGGEKYYVDSVKGRFTISRDNAG NSLYLQMNSLRAEDTAVYYCARDAM RGGDLDYWGQGTLVTVSS SEQ ID NO. 19 | EIVLTQSPSSLSASVGDRVTITCQASQ DIRNYLNWYQQKPGKAPKLLIYAASS LQSGVPSRFSGSGSGTDFTLTISSLQPE DFATYYCQQSYSTPGFGGGTKVDIK SEQ ID NO. 20 |
| C12 | QVQLVQSGGGLVQPGGSLRLSCAASG FTFTNFWMDWVRQAPGKGLEWVADI NKDGGEKYYVDSVKGRFTISRDNAG NSLYLQMNSLRAEDTAVYYCARDAM RGGDLDYWGQGTLVTVSS SEQ ID NO. 21 | AIQMTQSPSSLSASVGDRVTITCRASQ SISSYLNWYQQKPGKAPKLLIYAASSL QSGVPSRFSGSGSGTDFTLTISSLQPED FATYYCQQSYSTPTFGQGTKVEIK SEQ ID NO. 22 |
| D1 | EVQLVESGAEVKKPGASVKVSCKAS GYTFTGYYMHWVRQAPGQGPEWMG VISPSGDATTYAPKFQGRLTMTRETST GTDYMELSSLRSEDTAVYYCAKDLY WGAADYWGQGTLVTVSS SEQ ID NO. 23 | QSVLTQPASVSGSPGQSITISCTGTSGD VGGYNYVSWYQHHPGKAPKLMIFDV SDRPSGVSSRFFGSKSGNTASLTISGL QAEDEADYYCSSYTSSSTWVFGGGTK LTVL SEQ ID NO. 24 |
| D4 | EVQLVESGGGVVQPGGSLRLS CAASG FTFRTYAMHWVRQAPDKGLEWVAIIS DDETHKYYADSVKGRFTISRDNSKNT LFLQINGLRADDSAVYYCAVHDFDF WGQGTLVTVSS SEQ ID NO. 25 | QSVLTQPPSASGSPGQSVTISCTGTNS DIGGYNYVSWFQQHPGKAPKLMIYD VNKRPSGVPDRFSGSKSGNTASLTVS GLQAEDEADYYCSSFAGSNNSIFGTG TKLTVL SEQ ID NO. 26 |
| D6 | QMQLVQSGAEVKKPGASVKVSCKAS GYTFTGYYMHWVRQAPGQGLEWMG WINPNSGGTNYAQKFQGRVTITRDTS ASTAYMELSSLRSEDTAVYYCAREGE AVGLDLDYWGQGTLVTVSS SEQ ID NO. 27 | SYELTQPPSVSVAPGKTARITCGGNNI GSKSVHWYQQKPGQAPVLVIYYDSD RPSGIPERFSGSNSGNTATLTISRVEAG DEADYCQVWDSSSVVFGGGTQLTV L SEQ ID NO. 28 |
| D7 | QLQLQESGPGLVRPSETLSLTCTVSGG SISSFYWTWIRQPPGKALEWIGYIYHN GYSRYSPSLKSRVSMSVDTSRNQFSL HLNSVTAADTAVYYCARANNDYLFF DLWGRGTLVTVSS SEQ ID NO. 29 | QSVVTQPPSASGTPGQRVTISCSGSRS NIGSNIVSWYQHVPGTAPKLLIYGNA QRPSGVPDRFSGSKSGTSASLAISGLQ SEDEADYYCATWDDSLSGWVLGGGT KVTVL SEQ ID NO. 30 |

TABLE 5-continued

Heavy and Light Chain Variable Domain Amino Acid Sequences

| | Heavy chain variable domain regions | Light chain variable domain regions |
|---|---|---|
| D8 | EVQLVESGGGLVQPGGSLRLSCAASG FTFSSYEMNWVRQAPGKGLEWVSYIS SSGSTIYYADSVKGRFTISRDNAKNSL YLQMNSLRAEDTAVYYCARDGVDY YDSSGYYPYSAGMDVWGQGTTVTVS S SEQ ID NO. 31 | DIVMTQSPSTLSASVGDRVTITCRASQ SVDTWLAWYQQQPGKAPRLLISKAS RLQTDIPSRFSAGGSGTVFTLTISSLQP DDFATYYCQQYYSFPTFGQGTKLEIK SEQ ID NO. 32 |
| D10 | EVQLVESGGGLVKPGGSLRLSCAASG FTFSDYYMNWIRQAPGKGLEWVSYIS SGGTTIYYADSVKGRFTISRDNAKTSL FLQMDSLAIEDTAVYYCVRDFNSGSA FDLWGQGTMVTVSS SEQ ID NO. 33 | QPVLTQSPSVSVSPGQTGTITCSGDKL GDKYVAWYQQKSGQSPVLVIYQDNK RPSGIPERFSGSNSGNTATLTISGTQPV DEADYYCQAWDSSTVFGGGTKLTVL SEQ ID NO. 34 |
| E2 | EVQLVQSGAEVKKPGASVKVSCKAS GYTFTGYFMHWVRQAPGRVTMTRDT WINPDSGGTNYAQKFQGRVTMTRDT SISTAYMELNRLRSDDTAVYYCARDN TVRSDYWGQGTLVTVSS SEQ ID NO. 35 | QAVVTQPPSASGSPGQSITISCTGTSSD VGGYNYVSWYQQHPGKAPKLMIYD VSKRPSGVSNRFSGSKSGNTASLTISG LQAEDEADYYCSSYTSGTTRWVFGT GTKLTVL SEQ ID NO. 36 |
| E5 | QMQLVQSGAEVKKPGASVKVSCKAS EHTFTSYYMYWVRQAPGQGLEWMGI INPSDDYTNYAQKFQGRVTMTRDTST STVYMELSSLRSEDTAVYYCASFNGG GNSVFGALDIWGQGTMVTVSSSEQ ID NO. 37 | SSELTQDPAVSVASGQTVRITCQGDSL RRYYAGWYQQKPGQAPVLVIFGKNN RPSGIPDRFSGSSSGNTASLTITGAQAE DEADYYCNSRDSSGNHYVFGTGTKV TVL SEQ ID NO. 38 |
| E7 | EVQLVESGGGLVQPGRSLRLSCAASG FTFGDYAMHWVRQAPGKGLEWVSGI SWNSGSIGYADSVKGRFTISRDNAKN SLYLQMNSLRAEDTALYYCATGLGG WLRIDDAFDIWGQGTMVTVSS SEQ ID NO. 39 | SYELTQPPSVSVSPGQTARITCSGDAL PKQYAYWYQQKPGQAPVLVIYKDSE RPSGIPERFSGSSSGTTVTLTISGVQAE DEADYYCQSADSSGTYQVFGGGTKL TVL SEQ ID NO. 40 |
| F5 | QMQLVQSGAEVKKPGASVKVSCKAS GYTFTNYYLHWVRQAPGQGLEWMG MVNPIGGYTNYSQTFQGRVTVTRDTA TSTAYMELNSLRSEDTAVYFCARGFG FIDHWGQGTLVTVSS SEQ ID NO. 41 | LLVLTQSPSVSVSPGQTARITCSGDAL PKQYAYWYQQKPGQAPVLVIYKDSE RPSGIPERFSGSSSGTTVTLTISGVQAA DEADYYCQSADSSDIVVFGGGTQLTV L SEQ ID NO. 42 |
| F7 | QVQLVQSGGGLVQPGRSLRLSCAASG FTFDDYAMHWVRQAPGKGLEWVSGI SWNSGSIGYADSVKGRFTISRDNAKN SLYLQMNSLRAEDTALYYCAKDIKV ARGYGMDFWGQGTMVTVSS SEQ ID NO. 43 | QPVLTQPPSVSAAPGQMVTISCSGSSS NIGDNYVSWYQQFPGTAPKLLIYGDN RRPSAVPDRFSGSNSGTSASLAITGLQ AEDEADYYCQSYDRSLSGWVFGGGT KLTVL SEQ ID NO. 44 |
| F11 | QVQLQQSGPGLVKPSQTLSLTCAISGD NVSTNISSWNWIRQSPSRGLEWLGRT YYRSKWFNDYAVSVKSRITINPDTSK NLFSLQLNSVTPEDTAVYYCARGSAF NIWGQGTMVTVSS SEQ ID NO. 45 | SYVLTQPASVSGSPGQSITISCIGTSSD VGNSNLVSWYQHHPGKAPKLMIFEV TKRPSGVSNRFSGSKSGNTASLTISGL QAEDEADYYCSSYTSSSTLVFGGGTK VTVL SEQ ID NO. 46 |
| G1 | EVQLVQSGGGLVQPGGSLRLSCAASG FTFSDYYMNWIRQAPGKGLEWLSYIS SGGSTIYYADSVKGRFTISRDNAKNSL YLQMNSLRAEDTAVYYCAREDYGGN SVLFDYWGQGTLVTVSS SEQ ID NO. 47 | SSELTQDPAVSVALGQTVRITCQGDSL RSYYASWYQQKPGQAPVLVIYGKNN RPSGIPDRFSGSSSRNTASLTITGAQAE DEADYYCNSRDSSANHFYVFGTGTK VTVL SEQ ID NO. 48 |
| G2 | QVQLVQSGAEVKKPGASVKVSCKAS GYTFLSHYIHWVRQAPGQGLQWMGII NANGGSTTYAQEFLGRVIMTTDTSTG TAYLELISLRSDDTAVYYCARDMAGT WNHGSIDSWGQGTLVTVSS SEQ ID NO. 49 | LPVLTQPASVSGSPGQSITISCTGTSSD VGGYNYVSWYQQHPGKAPKLMIYD VSNRPSGVSNRFSGSKSGNTASLTISG LQAEDEADYYCSSYTSSSTYVFGTGT KLTVL SEQ ID NO. 50 |
| G3 | QMQLVQSGAEVKKPGASVKVSCKAS GYTFTGYYLYWVRQAPGQGLEWMG WIDPNSGGTNYAQKFQGRVTVTRDTS ISTAYMELTRLRSDDTAVYFCAIGYY GSTYFDYWGQGTLVTVSSG SEQ ID NO. 51 | QSVLTQPPSASATPGQRVTISCSGSTS NIGTNAVDWYQQPPGTAPKLLIFSNN QRPSGVPDRFSGSKSGTSASLAISGLQ SEDEADYYCAAWDDSLNGYVFGTGT KVTVL SEQ ID NO. 52 |

TABLE 5-continued

Heavy and Light Chain Variable Domain Amino Acid Sequences

| | Heavy chain variable domain regions | Light chain variable domain regions |
|---|---|---|
| G5 | QVQLVQSGAEVKKPGASVKVSCKAS GYTFTNYYMHWVRQAPGQGLEWMG IMDPSGGSATYAQKLQGRIIMTRDTST STVYMELSNLRSEDTAVYYCARDPDF YGLGSYSHGAFDIWGQGTMVTVSS SEQ ID NO. 53 | QPVLTQPASVSGSPGQSVTISCTGAGS DVGGYDYVSWYQQHPGKAPKLIIFD VNNRPSGVSYRFSGSKSANTASLTISG LQSEDEADYYCSSYTSSSTWVFGGGT KLTVL SEQ ID NO. 54 |
| G6 | QMQLVQSGAEVKKPGESLKISCKGSG YNFTNYFIAWVRQMPGKGLEWMGM FYPGDSKTTYNPSFQGQVIISADKSINT AYLQWSSLKASDTAVYYCARAFYAA GNYFDYWGQGTLVTVSSG SEQ ID NO. 55 | SSELTQDPAVSVALGQTVRITCQGDSL RRYYASWYQQKPGQAPRLLMYGKNI RPSGIPDRFSGTDSGNTAFLTITGAQA EDEADYYCNSRDTNANQPLVLFGGG TKVTVL SEQ ID NO. 56 |
| G8 | QVQLVQSGAEVKKPGASVKVSCKAS GYTFTGYYMHWVRQAPGQGLEWMG WINPNSGGTNYAQKFQGRVTMTRDT SISTAYMELSRLRSDDTAVYYCASNY YGSGSSFDYWGQGTLVTVSS SEQ ID NO. 57 | QPVLTQPRSVSGSPGQSVTISCTGTSS DVGGYNFVSWYQQHPGKAPKLMIYD VSKRPSGVSNRFSGSKSGNTASLTISG LQAEDEADYYCNSYTSSSTRYVFGTG TKLTVL SEQ ID NO. 58 |
| G12 | QVQLVQSGADVKKPGASVKVSCKAS GYTFTSYYMHWVRQAPGQGLEWMG IINPSGGSTSYAQKFQGRVTMTRDTST STVYMELSSLRSEDTAVYYCARGVGE LWGWGQGTLVTVSS SEQ ID NO. 59 | QSVLTQPASVSGYPGQSITISCIGSSSD VGFSQYVSWYQHHPDRPPKLIIYDVS NRPSGVSDRFSGSKSGNTASLTISGLQ AEDEADYYCSSYRSSGTYVFGTGTKV TVL SEQ ID NO. 60 |
| H4 | QVQLVESGGGLVKPGRSLRLSCTASG FTFGDYAMSWFRQAPGKGLEWVGFI RSKAFGGTTEYAASVKGRFSISRDDS KNIAYVQMNSLKTDDTAVYYCTRDS GPGWERSFDYWGQGTLVTVSS SEQ ID NO. 61 | QSVLTQPPSVSVAPGKTARITCGGNNI GSKSVHWYQQKPGQAPVLVIYYDSD RPSGIPERFSGSNSGNTATLTISRVEAG DEADYYCQVWDSSSDHPVFGGGTQL TVL SEQ ID NO. 62 |
| H7 | EVQLVESGAEVKKPGASVKVSCKAS GYTFTGYYMHWVRQAPGQGLEWMG WINPNSGGTNYAQKFQGRVTMTRDT SISTAYMELSRLRSDDTAVYYCARDI VGSTDYWGQGTLVTVSS SEQ ID NO. 63 | QAVLTQPASVSGSPGQSITISCTGTNS DIGTYNYVSWYQQHPGKAPKLIIYDV TKRPSGVSNRFSGSKSGNTASLTISGL QAEDEADYYCSSYTSSSTRWVFGGGT QLTVL SEQ ID NO. 64 |
| H8 | EVQLVESGAEVKKPGASVKVSCKAS GYTFTGYYMHWVRQAPGQGLEWMG WIDPNSGGTNYAQKFQGRVTMTRDT SISTAYMELSRLRSDDTAVYYCAKDD YWGQGTLVTVSS SEQ ID NO. 65 | QAGLTQPASVSGSPGQSIAISCTGTSS DVGSYNLVSWYQQHPGKAPKLMIYE VIKRPSGISDRFSGSKSGNTASLTISGL QAEDEADYYCFSYTSSTTRYVFGTGT KVTVL SEQ ID NO. 66 |
| H10 | QVQLVQSGAEVKKPGASVKVSCKTS GYTFTSYNMHWVRQAPGQGLEWMG VINPSDRYTWYAQKFRGRVTMTRDT STSTVYMELSSLRSEDTAIYYCARGGE DTASYYWGQGTLVTVSS SEQ ID NO. 67 | SSELTQDPAVSVALGQTLRITCQGDSL RSYYASWYQQKPGQAPVLVIYGKNN RPSGIPDRFSGSTSGNTDSLTITGAQAE DEADYFCSSRDSSDNHLNVLFGGGTK VTVL SEQ ID NO. 68 |
| H11 | QVQLVQSGAEVKKPGASVKVSCKAS GYTFTTYYMHWVRQAPGQGLEWMG IINPTGGSTSYAQKFQGRVTMTRDTST STVYMELSSLRSEDTAVYYCARTEYS SGWAGDYWGQGTLVTVSS SEQ ID NO. 69 | QSVLTQPPSVSGSPGQSITISCTGTSRD VGLYNYVSWYQQHPDKAPKLLIYDV SERPSGISNRFSGSKSGNTATLTISGLQ PEDEADYYCGS YTSSSTRYVFGTGTK VTVL SEQ ID NO. 70 |
| C3sh1A11 | QVQLVQSGAEVKKPGASVKVSCKAS GYTFTGYYMHWVRQAPGQGLEWMG WINPNSGGTNYAQKFQGRVTMTRDT SISTAYMELSRLRSDDTAVYYCAREG VGATSWFDPWGQGTLVTVSS SEQ ID NO. 71 | SSELTQDPAVSVALGQTVRITCQGDSL RRYHASWYQQKPGQAPVLVIYNKNN RPSGIPDRFSGSSSGNTDSLTITGAQAE DEADYYCNSRDSSGNYVFGTGTKLT VL SEQ ID NO. 72 |
| C3sh1A2 | EVQLVQSGGGVVQPGRSLRLSCAASG FTFSSYAMHWVRQAPGKGLEWVAA MSHDGIQKDYADSVKGRFTISRDNSK NTLYLQMNSLRAEDTAVYYCAQGGG FAYGMEDYWGQGTLVTVSS SEQ ID NO. 73 | AIQMTQSPSSLSASVGDRVSFTCQASQ DISNYLNWYQQKPGKAPKLMISDAST LETGVPSRFSGSGSGTYFTFTISSLQPD DFATYYCQHYDSPPLTFGGGTKVEIK SEQ ID NO. 74 |

TABLE 5-continued

Heavy and Light Chain Variable Domain Amino Acid Sequences

| | Heavy chain variable domain regions | Light chain variable domain regions |
|---|---|---|
| C3sh1A5 | QVQLVQSGAEEKTPGASVKISCKASG NTFNNYDIHWVRQAPGERPEWMGWI NSGNGDTRNSQKFQGRVTITWDTSAS TAYMELSSLTSEDTGVYFCARAEGPL DYWGQGTLVTVSS SEQ ID NO. 75 | DIVMTQTPSSLSASVGDRVTITCRASQ GIYNYLAWYQQKLGKAPNLLIYATSN LQSGVPSRFSGSGSGTDFLTISSLQPE DFATYYCQQSYSTPWTFGQGTKVEIK SEQ ID NO. 76 |
| C3sh1A9 | QVQLVQSGAEVKKPGASVKVSCKAS GYTFTSKWMHWVRQAPGQGPEWMG VINPSSGGTTYAQKFQGRLTVTRDTSS STVYMELSSLRSEDTAVYYCARDDVF DYYFGLDVWGQGTTVTVSS SEQ ID NO. 77 | SSELTQDPAVSVALGQTVRITCQGDSL RRYYASWYQQKPGQAPRLLIYGKNIR PSGIPDRFSGTDSGNTDFLTITGAQAE DEADYYCNSRDTDANQPLVLFGGGT KLTVL SEQ ID NO. 78 |
| C3sh1B2 | QVQLVQSGGDLVQPGGSLRLSCAASG FLFSNSWMTWVRQAPGKGLEWLANI KPDGSGQYYVDSLRGRFTISRDNAKN SLYLQMNSLRVEDTAMYYCARDRGN DGLDYWGQGTLVTVSS SEQ ID NO. 79 | SYELTQPPSVSVSPGQTARITCSGEKL DDKYTFWYQQRTGQTPVLVIYQDKK RPSGIPERFSGSNSGNTATLTISGTQAV DEADYYCQTYDSGAPVFGGGTKLTV L SEQ ID NO. 80 |
| C3sh1B4 | EVQLVESGAELKKPGASVKVSCMAS GYTFTDYYMHWVRQAPGQGLEWMG WINPNSGGTNYAQKFQGRVTMTRDT SISTAYMELSRLRSDDTAVYYCARDG STYTDYWGQGTLVTVSS SEQ ID NO. 81 | QSVLTQPASVSGSPGQSITISCTGTSSD VGGYDFVAWYQQHPGKAPKLLIYDV SNRPSGVSNRFSGSKSGNTASLKISGL RAEDEADYYCSSYTSSSARWVFGGGT KVTVL SEQ ID NO. 82 |
| C3 | QLVESGGGLVKPGRSLRLSCTASG FTFGDYAMSWFRQAPGKGLEWVGFI RSKAFGGTTEYAASVKGRFTISRDDS NSIAYLQMNSLKTEDTAVYYCTRDSG PGWERSFDYWGQGTLVTVSS SEQ ID NO. 83 | SYELTQPPSVSVAPGKTARITCGGNNI GSKSVHWYQQKPGQAPVLVIYYDSD RPSGIPERFSGSNSGNTATLTISRVEAG DEADYYCQVWDSSSDHPVFGGGTKL TVL SEQ ID NO. 84 |
| C3sh1B9 | QVQLVQSGAEEKTPGASVKISCKASG NTFNNYDIHWVRQAPGERPEWMGWI NSGNGDTRNSQKFQGRVTITWDTSAS TAYMELSSLTSEDTGVYFCARAEGPL DYWGQGTLVTVSS SEQ ID NO. 85 | DIVMTQSPSSLSASVGDRVTITCRASQ GIYNYLAWYQQKLGKAPNLLIYATSN LQSGVPSRFSGSGSGTDFLTISSLQPE DFATYYCQQSYSTPWTFGQGTKVEIK SEQ ID NO. 86 |
| C3sh1C1 | EVQLVQSGAEVKKPGASVKVSCKAS GYTFTGYYMHWVRQAPGQSPEWMG WINVGNGNIRYSQKFQGRVTFTGDTS ATTAYMDLSSLRSEDTAVFYCAREGA ASGLDLDYWGQGTLVTVSS SEQ ID NO. 87 | SYELTQPPSVSVAPGKTARITCGGNNI GSKHVHWYQQKPGQAPVLVINYDSD RPSGIPERLSGSNSGNTATLTISRVEAG DEADYYCQVWDSTSDHVIFGGGTKL TVL SEQ ID NO. 88 |
| C3sh1C2 | EVQLLESGGGVVQPGRSLRLSCAASG FTFSNYAMHWVRQAPGKGLEWVAVI SLDGSNRHYADSVKGRFTISRDNSQN TLYLQMNSLRAEDTAMYYCAQDLYD DNRWGVFDYWGQGTLVTVSS SEQ ID NO. 89 | QSVLTQPPSVSVAPGKTARITCGGNNI GSKSVHWYQQKPGQAPVLVIYYDSD RPSGIPERFSGSNSGNTATLTISRVEAG DEADYYCQVWDSSSDHVFGGGTKL TVL SEQ ID NO. 90 |
| C3sh1C7 | EVQLLESGAEVKKPGASVKVSCKASG YTFTSYYMHWVRQAPGQGLEWMGII NPSGGSTSYAQKFQGRVTMTRDTSTS TVYMELSSLRSEDTAVYYCARDPGA GGYFDYWGQGTLVTVSS SEQ ID NO. 91 | SYVLTQPPSASGSPGQSVTISCTGTSSD VGGYNYVSWYQQHPGKAPKLMIYD VSKRPSGVPDRFSGSKSGNTASLTISG LQAEDEADYYC TKLTVL SEQ ID NO. 92 |
| C3sh1D11 | QVQLVQSGAEMKKPGSSVKVSCKAS GYTFTSYGISWVRQAPGQGLEWMGW ISAYNGNTNYAQKLQGRVTMTTDTST STAYMELRSLRSDDTAVYYCARDLSQ WYQLYGADYYYGMDVWGQGTTVT VSS SEQ ID NO. 93 | QSALTQPPSVSAAPGQKVTISCSGSSS NIGNNYVSWYQQLPGTAPKLLIYDNN KRPSGIPDRFSGSKSGTSATLGITGLQT GDEADYYCGTWDSSLSAVVFGGGTK VTVL SEQ ID NO. 94 |
| C3sh1D4 | EVQLVQSGAEVTKPGASVKVSCKAS GYTFTGYYMHWVRQAPGQGLEWMG WINPNSGGTNYAQKFQGRVTMTRDT SISTAYMELSRLRSDDTAVYYCARDN AGLGDYWGQGTLVTVSS SEQ ID NO. 95 | QAGLTQPASVSVSPGQSITISCTGTSSD VGAYNYVSWYQQHPGKAPKLMIYD VSNRPSGVSNRFSGSKSGNTASLTISG LQAEDEADYYCSSYSSINSRYVFGTG TKVTVL SEQ ID NO. 96 |

TABLE 5-continued

Heavy and Light Chain Variable Domain Amino Acid Sequences

| | Heavy chain variable domain regions | Light chain variable domain regions |
|---|---|---|
| C3sh1D6 | EVQLVESGAEVKKPGSSVKVSCKASG GTFSSYAISWVRQAPGQGLEWMGIIN PSGGSTSYAQKFQGRVTMTRDTSTST VYMELSSLRSEDTAVYYCAGTPSLKY DYYYGMDVWGQGTTVTVSS SEQ ID NO. 97 | QSVLTQPASVSGSPGQSITISCTGTSSD VGGYNYVSWYQQYPGKAPKLMIYD VSKRPSGVSHRFSGSKSGNTASLTISG LQAEDEADYYCSSYTSSSTLVFGGGT KLTVL SEQ ID NO. 98 |
| C3sh1E12 | EVQLVESGAEVKKPGASVKVSCKAS GYTFTNYYIHWVRQAPGQGLEWMGII NPSGGYTSSAQKFQGRVTMTRDTSTS TVYMELSSLRSEDTAVYYCARDRDSG SYYDAFDIWGQGTMVTVSS SEQ ID NO. 99 | SSELTQDPAVSVALGQTVRITCQGDSL RSYYASWYQQKPGQAPLLVIYGKNN RPAGISDRFSGSDSEDIASLTITGAQAE DEADYYCNSRDSNAHWVFGGGTKLT VL SEQ ID NO. 100 |
| C3sh1E7 | QVQLVQSGGGLVQPGGSLRLSCAASG FTFSSSAMSWVRQAPGKGLEWVSGIS GSGDSAYYADSVKGRFTISRDNSKNT LYLHMNSLTAEDTAVYYCASGGNYG SGTIVSHGMDVWGQGTTVTVSS SEQ ID NO. 101 | QSVVTQPPSVSAAPGHKVTISCSGNSS NVGRNYVSWYQQVPGTAPKLLIYDD NKRPSGIPDRFSGSTSGASATLVITGL QTGDEADYYCGAWDSSLSAGVFGGG TKLTVL SEQ ID NO. 102 |
| C3sh1E9 | EVQLLESGGGLVQPGGSLRLS CAASG FTFNNYAMSWVRQAPGKGLEWVSTI SGSGENTHYADSVKGRFTISRDNSKD TLYLQMSSLRAEDTAVYYCANQYDT TDYYYWGEYFHHWGQGTLVTVSS SEQ ID NO. 103 | SYELTQPPSVSVSPGQTARITCSGDAL PKQYAYWYQQKPGQAPVLVIYKDSE RPSGIPERFSGSSSGTTVTLTISGVQAE DEADYYCQS AD S TVL SEQ ID NO. 104 |
| C3sh1F1 | EVQLVESGAEVKKPGASVKVSCKAS GYTFTGYYMHWVRQAPGQGLEWMG WINPNSGGTNYAQKFQGRVTMTRDT STSTVYMELSSLRSEDTAVYYCARDI RAFDIWGQGTMVTVSS SEQ ID NO. 105 | QPVLTQPASVSGSPGQSITISCTGTSSD VGSYNFVSWYQQHPGKAPKLMIYDV SNRPSGVSDRFSGSKSGNTASLTISGL QAEDEADYYCSSYTSSSTRWVFGGGT KLTVL SEQ ID NO. 106 |
| C3sh1F10 | EVQLVQSGVEVKKPGASVKVSCKVS GNTLTEISMHWVRQVPGKGLEWMGG FDLEDGETVYAQKFQGRVTLTEDTSI DTAYELRSLRSEDTAVYYCATGPAGY RLFEYWGQGTLVTVSS SEQ ID NO. 107 | LPVLTQPPSVSGAPGQRVTISCTGSSS NIGAGYDVHWYQQLPGTAPKLLIYG NSNRPSGVPDRFSGSKSGTSASLAITG LQAEDEADYYCQSYDSSLSGYVFGTG TKVTVL SEQ ID NO. 108 |
| C3sh1F12 | EVQLVQSGAEVKKPGASVKVSCKAS GYTFTSHYMHWVRQAPGQGLEWMG VINPSGGTSYAQKFQGRVTMTRDTS TSTVYMDLSSLRSEDTAVYYCARRSE AYYHGMDVWGQGTTVTVSS SEQ ID NO. 109 | QSVLTQPPSASGTPGQRVTISCSGSSS NIGSNTVNWYQQLPGTAPKLLIYSNN QRPSGVPDRFSGSKSGTSASLAISGLQ SEDEADYYCAAWDDSLNGWVFGGG TKLTVL SEQ ID NO. 110 |
| C3sh1F2 | EVQLVESGGGLVKPGESLRLS CAASG FTFKSYPMAWVRQAPGKGLEWVSSIS SSGDHRYYADSVKGRFTISRDNARNS LSLQMNNLRAEDTAVYYCPAGRDFD HWGRGTLVTVSS SEQ ID NO. 111 | DIVMTQTPLSLPVTPGEPASISCRSSQS LLYSNGYNYLDWYLQKPGQSPQLLIY WGSNRASGVPDRFSGSGSGTDFTLKIS RVEAEDVGIYYCMQALHVPPYTFGQ GTKVEIK SEQ ID NO. 112 |
| C3sh1G1 | QVQLVESGAEVKKPGASVKVSCKAS GYTFTDYYIHWVRQAPGQGLEWVG WINPNSGGTNYAQRFQGRVTMTRDT SISTTYMELSRLRFDDTAVYYCASDP GGNPYFDYWGQGTLVTVSS SEQ ID NO. 113 | SYELTQPPSVSVAPGKTATITCGGDTI GSKVVHWYQQKPGQAPVLMYYDS ERPSGIPERFSASNSGNTATLTISRVEA GDEADYYCQVWDSGSVVFGGGTKLT VL SEQ ID NO. 114 |
| C3sh1G11 | EVQLVESGGGVVQPGRSLRLSCAASG FTFSSYGMHWVRQAPGKGLEWVALI SYDGTNKYYADSVKGRFTISRDNSKN TLYLQMNSLSSEDTALYYCASNHDIL TGGDYWGQGTLVTVSS SEQ ID NO. 115 | SYELTQPPSASGTPGQRVTISCSGSSSN IGPYSINWYQQLPGTAPKLLIHSNTQR PSGVPDRFSGSKSGTSASLAISGLQSE DEADYYCAAWDGSLNGVVFGGGTQ LTVL SEQ ID NO. 116 |
| C3sh1G2 | EVQLVESGGALVQPGGSLRLSCAGSG FTFSNFWMHWVRQAPGKGLEWVADI SGDGSEKYYVDSVKGRFTFSRDNARN SLYLQMNSLRIEDTAVYYCARDAMR GGDLDYWGQGTLVTVSS SEQ ID NO. 117 | DIVMTQTPSSLSASVGDRVTITCRASQ SISSYLNWYQQKPGKAPKLLIYAASSL QSGVPSRFSGSGSGTDFTLTISSLQPED FATYYCQQSYSTPHFGGGTKVEIK SEQ ID NO. 118 |

TABLE 5-continued

Heavy and Light Chain Variable Domain Amino Acid Sequences

| | Heavy chain variable domain regions | Light chain variable domain regions |
|---|---|---|
| C3sh1G3 | EVQLVQSGAEVKKPGSSVKVSCKASG GTFSSYAISWVRQAPGQGLEWMGGII PIFGTANYAQKFQGRVTITADESTSTA YMELSSLRSEDTAVYYCAGRFDYDS SGYYYGPFDYWGQGTLVTVSS SEQ ID NO. 119 | QSVVTQPPSVSAAPGHKVTISCSGNSS NVGRNYVSWYQQVPGTAPKLLIYDD NKRPSGIPDRFSGSQSGTSATLGITGL QTGDEADYYCGTWDSSLTLYVFGTG TKLTVL SEQ ID NO. 120 |
| C3sh1G5 | EVQLVQSGAEVKKPGESLKISCKGSG YSFTSYWIGWVRQMPGKGLEWMGII YPGDSDTIYSPSFQGQVTLSADKSTST AYVQWNSLKASDTAVYYCARLTVSG SSTTTGGMDVWGHGTTVTVSS SEQ ID NO. 121 | QSVVTQPPSVSAAPGQKVTISCSGSDS NIGNNYVSWYQQVPGTAPKLLIYDNY KRPSGIPDRFSGSKSGTSATLGITGLQT GDEADYYCVTGDGGLGAVVFGGGTK LTVL SEQ ID NO. 122 |
| C3sh1G8 | QVQLVQSGAEVKKPGASVKVSCKTS GYNFNTYYIHWVRQAPGQGLEWMGI INPSGGYTSYAQNFQGRVTMTRDTST STVYMELSSLRSEDTALYYCARELGG NVRRDDAFDIWGQGTMVTVSS SEQ ID NO. 123 | SSELTQDPAVSVALGQTVRITCQGDSL RRYYASWYQQKPGQAPLLVMFGEDK RPSGIPDRFSGSSSGNTASLTITGAQAE DEADYYCNSRDTSGSWVFGGGTKLT VL SEQ ID NO. 124 |
| C3sh1H10 | QMQLVQSGAEVKKPGASVKVSCKAS GYTFTSYYLHWVRQAPGQGLEWMGI IHSSGGSTTYAQKFQGRVTMTRDTST STVYMELSSLRSEDTAVYYCARGYFG SGSFDYWGHGTLVTVSS SEQ ID NO. 125 | QSVLTQPASVSGSPGQSITISCTGTSSD VGGYNYVSWYQQHPGKAPKLMIYD VSNRPSGVSNRFSGSKSGNTASLTISG LQAEDEADYYCSSYTSSSTYVFGTGT KLTVL SEQ ID NO. 126 |
| C3sh1H4 | QVQLVQSGAEVKQPGASVKVSCKAS GYTFTNNYMHWVRQAPGQGLEWMG IINPTGGSTTYAQKFQGRVIMTTDTST STVFMELSSLRSEDTAVYYCARDLGE LLLAFDYWGQGTLVTVSS SEQ ID NO. 127 | SYVLTQPASVSGSPGQSITISCTGTSSD VGGYNYVSWYQQHPGKAPKLMIYD VSKRPSGVSNRFSGSKSGNTASLTISG LQAEDEADYYCSSYTSSSTLVFGTGT KVTVL SEQ ID NO. 128 |
| MA8 | QMQLVQSGAEVKKPGASVKVSCKAS GYRFGGYYMHWVRQAPGQGLEWM GWINPNSGGTNYAQKFQGRVTITRDT SASTAYMELSSLRSEDTAVYYCAREG EAVGLDLDYWGQGTLVTVSS SEQ ID NO. 129 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MB1 | QMQLVQSGAEVKKPGASVKVSCKAS GYGMKGYYMHWVRQAPGQGLEWM GWINPNSGGTNYAQKFQGRVTITRDT SASTAYMELSSLRSEDTAVYYCAREG EAVGLDLDLWGQGTLVTVSS SEQ ID NO. 130 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MB3 | QMQLVQSGAEVKKPGASVKVSCKAS GYQMRGYYMHWVRQAPGQGLEWM GWINPNSGGTNYAQKFQGRVTITRDT SASTAYMELSSLRSEDTAVYYCAREG EAVGLDLDYWGQGTLVTVSS SEQ ID NO. 131 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MB10 | QMQLVQSGAEVKKPGASVKVSCKAS GYLMQGYYMHWVRQAPGQGLEWM GWINPNSGGTNYAQKFQGRVTITRDT SASTAYMELSSLRSEDTAVYYCAREG EAVGLDLDYWGQGTLVTVSS SEQ ID NO. 132 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MB12 | QMQLVQSGAEVKKPGASVKVSCKAS GYSLEGYYMHWVRQAPGQGLEWMG WINPNSGGTNYAQKFQGRVTITRDTS ASTAYMELSSLRSEDTAVYYCAREGE AVGLDLDYWGQGTLVTVSS SEQ ID NO. 133 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MC8 | QMQLVQSGAEVKKPGASVKVSCKAS GYMPDGYYMHWVRQAPGQGLEWM | SYELTQPPSVSVAPGKTARITCGGNNI GSKSVHWYQQKPGQAPVLVIYYDSD |

TABLE 5-continued

Heavy and Light Chain Variable Domain Amino Acid Sequences

| | Heavy chain variable domain regions | Light chain variable domain regions |
|---|---|---|
| | GWINPRTGGTNYAQKFQGRVTITRDT SASTAYMELSSLRSEDTAVYYCAREG AAFRLELDAWGQGTLVTVSS SEQ ID NO. 134 | RPSGIPERFSGSNSGNTATLTISRVEAG DEADYYCQVWDSSSVVFGGGTQLTV L SEQ ID NO. 28 |
| MD1 | QMQLVQSGAEVKKPGASVKVSCKAS GYRLQGYYMHWVRQAPGQGLEWM GWINPNSGGTNYAQKFQGRVTITRDT SASTAYMELSSLRSEDTAVYYCAREG EAVGLDLDYWGQGTLVTVSS SEQ ID NO. 135 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MD4 | QMQLVQSGAEVKKPGASVKVSCKAS GYNWTGYYMHWVRQAPGQGLEWM GWINPMAGGTNYAQKFQGRVTITRD TSASTAYMELSSLRSEDTAVYYCARE GWARGVELDMWGQGTLVTVSS SEQ ID NO. 136 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSA11 | QMQLVQSGAEVKKPGASVKVSCKAS GYSFTGYYMHWVRQAPGQGLEWMG WVNPKSGGTNYAQKFQGRVTITRDTS ASTAYMELSSLRSEDTAVYYCAREG WARRIDLDEWGQGTLVTVSS SEQ ID NO. 137 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSB7 | QMQLVQSGAEVKKPGASVKVSCKAS GYSFSGYYMHWVRQAPGQGLEWMG WVNPMSGGTNYAQKFQGRVTITRDT SASTAYMELSSLRSEDTAVYYCAREG MAMRLELDKWGQGTLVTVSS SEQ ID NO. 138 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSD2 | QMQLVQSGAEVKKPGASVKVSCKAS GYNFAGYYMHWVRQAPGQGLEWM GWVNPQSGGTNYAQKFQGRVTITRD TSASTAYMELSSLRSEDTAVYYCARE GEGRGLDLDWWGQGTLVTVSS SEQ ID NO. 139 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSE3 | QMQLVQSGAEVKKPGASVKVSCKAS GYNFSGYYMHWVRQAPGQGLEWMG WINPKSGGTNYAQKFQGRVTITRDTS ASTAYMELSSLRSEDTAVYYCAREGG ARGVDLDTWGQATLVTVSS SEQ ID NO. 140 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSE5 | QMQLVQSGAEVKKPGASVKVSCKAS GYSFGGYYMHWVRQAPGQGLEWMG WVNPNSGGTNYAQKFQGRVTITRDTS ASTAYMELSSLRSEDTAVYYCAREGY GLGLDLDVWGQGTLVTVSS SEQ ID NO. 141 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSC8 | QMQLVQSGAEVKKPGASVKVSCKAS GYNFGGYYMHWVRQAPGQGLEWM GWVNPKSGGTNYAQKFQGRVTITRD TSASTAYMELSSLRSEDTAVYYCARE GEAVGLDLDYWGQGTLVTVSS SEQ ID NO. 142 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |
| MSH1 | QMQLVQSGAEVKKPGASVKVSCKAS GYNFGGYYMHWVRQAPGQGLEWM GWVNPHSGGTNYAQKFQGRVTITRD TSASTAYMELSSLRSEDTAVYYCARE GEAWGLDLDLWGQGTLVTVSS SEQ ID NO. 143 | SYELTQPPSVSVAPGKTARITCGGNNI GSKSVHWYQQKPGQAPVLVIYYDSD RPSGIPERFSGSNSGNTATLTISRVEAG DEADYYCQVWDSSSVVFGGGTQLTV L SEQ ID NO. 28 |

INCORPORATION BY REFERENCE

The contents of all references, patents, pending patent applications and published patents, cited throughout this application are hereby expressly incorporated by reference.

We claim:

1. A recombinant fully human anti-CD137 antibody that specifically binds to human CD137, wherein the antibody comprises:
   a heavy chain variable domain comprising the amino acid sequence of SEQ ID NO. 137 or SEQ ID NO. 143; and
   a light chain variable domain comprising the amino acid sequence of SEQ ID NO. 28.

2. The recombinant fully human anti-CD137 antibody of claim 1, wherein the antibody comprises heavy chain/light chain variable domain amino acid sequences selected from the group consisting of SEQ ID NO. 137/SEQ ID NO. 28 and SEQ ID NO. 143/SEQ ID NO. 28.

3. The recombinant fully human anti-CD137 antibody of claim 1, wherein the antibody is classified as an isotype selected from the group consisting of: IgG, IgM, IgD, IgA, and IgE.

4. The recombinant fully human anti-CD137 antibody of claim 3, wherein the antibody is an IgG1 or an IgG4.

5. A recombinant fully human anti-CD137 antibody Fab fragment that specifically binds to human CD137, wherein the Fab fragment comprises:
   a heavy chain variable domain comprising the amino acid sequence of SEQ ID NO. 137 or SEQ ID NO. 143; and
   a light chain variable domain comprising the amino acid sequence of SEQ ID NO. 28.

6. The recombinant fully human anti-CD137 antibody Fab fragment of claim 5, wherein the Fab fragment comprises heavy chain/light chain variable domain amino acid sequences selected from the group consisting of SEQ ID NO. 137/SEQ ID NO. 28 and SEQ ID NO. 143/SEQ ID NO. 28.

7. The recombinant fully human anti-CD137 antibody Fab fragment of claim 5, wherein the fragment is classified as an isotype selected from the group consisting of: IgG, IgM, IgD, IgA, and IgE.

8. The recombinant fully human anti-CD137 antibody Fab fragment of claim 7, wherein the fragment is an IgG1 or an IgG4.

9. A recombinant anti-CD137 antibody, or an antigen-binding fragment thereof, that specifically binds to human CD137, comprising:
   a heavy chain variable domain comprising complementarity determining regions (CDRs) as set forth in a heavy chain variable domain amino acid sequence selected from the group consisting of SEQ ID NO. 137, and SEQ ID NO. 143;
   and a light chain variable domain comprising the amino acid sequence of SEQ ID NO. 28.

10. The recombinant anti-CD137 antibody, or antigen-binding fragment thereof, of claim 9, comprising heavy/light chain variable domain amino acid sequences selected from the group consisting of SEQ ID NO. 137/SEQ ID NO. 28 and SEQ ID NO. 143/SEQ ID NO. 28.

11. The recombinant anti-CD137 antibody, or antigen-binding fragment thereof, of claim 9, wherein the antibody, or antigen-binding fragment thereof, is classified as an isotype selected from the group consisting of: IgG, IgM, IgD, IgA, and IgE.

12. The recombinant anti-CD137 antibody, or antigen-binding fragment thereof, of claim 11, wherein the antibody is an IgG1 or an IgG4.

13. The recombinant anti-CD137 antibody, or antigen-binding fragment thereof, of claim 9, wherein antibody, or antigen-binding fragment is an Fab, an Fab', an F(ab')2, an Fv, a single-chain antibody (scFv), a diabody, a triabody or a tetrabody.

14. The recombinant anti-CD137 antigen-binding fragment of claim 13, which is a single chain antibody (scFv).

15. The recombinant anti-CD137 antibody, or antigen-binding fragment thereof, of claim 9, wherein the antibody, or antigen-binding fragment thereof, comprises a heavy chain variable domain and a light chain variable domain selected from the group consisting of
   a) a heavy chain variable domain comprising the CDRs as set forth in SEQ ID NO. 137 and comprising the amino acid sequence of SEQ ID NO. 137, and a light chain variable domain comprising the CDRs as set forth in SEQ ID NO. 28 and comprising the amino acid sequence of SEQ ID NO. 28; and
   b) a heavy chain variable domain comprising the CDRs as set forth in SEQ ID NO. 143 and the amino acid sequence of SEQ ID NO. 143, and comprising a light chain variable domain comprising the CDRs as set forth in SEQ ID NO. 28 and the amino acid sequence of SEQ ID NO. 28.

16. The recombinant anti-CD137 antibody, or antigen-binding fragment thereof, of claim 15, which is a Fab fragment or a single chain antibody (scFv).

17. A single chain anti-CD137 antibody that specifically binds to human CD137, comprising:
   a heavy chain variable domain comprising the amino acid sequence of SEQ ID NO. 137 or SEQ ID NO. 143; and
   a light chain variable domain comprising the amino acid sequence of SEQ ID NO. 28,
   wherein the heavy chain variable domain and the light chain variable domain are connected by a peptide linker.

18. The single chain anti-CD137 antibody of claim 17, comprising heavy chain/light chain variable domain amino acid sequences selected from the group consisting of SEQ ID NO. 137/SEQ ID NO. 28 and SEQ ID NO. 143/SEQ ID NO. 28.

19. A pharmaceutical composition comprising the recombinant anti-CD137 antibody, antigen-binding fragment thereof, the anti-CD137 antibody Fab fragment or the single chain anti-CD137 antibody, of any one of claims 1-16, and a pharmaceutically acceptable carrier.

\* \* \* \* \*

SEQUENCE LISTING

<160> NUMBER OF SEQ ID NOS: 145

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Val Pro Thr Asp Gly Tyr Asn Tyr Phe Gly Ala Phe Asp Ile Trp
            100                 105                 110

Gly Gln Gly Thr Met Val Thr Val Ser Ser
        115                 120

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ala Gly Leu Thr Gln Pro Pro Ser Val Ser Glu Ala Pro Arg Gln
1               5                   10                  15

Arg Val Thr Ile Ser Cys Ser Gly Ser Tyr Ser Asn Ile Gly Phe Asn
            20                  25                  30

Ala Val Ser Trp Tyr Gln Gln Phe Pro Gly Glu Ala Pro Lys Leu Leu
        35                  40                  45

Ile Tyr Tyr Asp Asp Leu Leu Ser Ser Gly Val Ser Gly Arg Phe Ser
    50                  55                  60

Gly Ser Arg Ser Gly Thr Ser Ala Ser Leu Ala Ile Ser Gly Leu Gln
65                  70                  75                  80

Ser Asp Asp Glu Ala Val Tyr Tyr Cys Ala Thr Trp Asp Asp Ser Val
                85                  90                  95

Asn Gly Trp Val Phe Gly Gly Gly Thr Lys Leu Thr Val Leu
            100                 105                 110

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Glu Val Gln Leu Val Gln Ser Gly Gly Asp Leu Val Arg Pro Gly Gly
1               5                   10                  15

Ser Leu Arg Leu Ser Cys Thr Val Ser Gly Leu Pro Tyr Ser Asp Tyr
            20                  25                  30

Tyr Met His Trp Ile Arg Gln Ala Pro Gly Lys Lys Leu Glu Trp Ile
            35                  40                  45

Ser Asp Ile Gly Pro Arg Gly Thr Ser Val His Tyr Ala Asp Ser Val
50                  55                  60

Lys Gly Arg Phe Thr Val Ser Arg Asp Asn Thr Lys Asn Ser Leu Tyr
65                  70                  75                  80

Leu Gln Met Asn Asn Leu Arg Ala Asp Asp Thr Ala Val Tyr Tyr Cys
            85                  90                  95

Ala Asn Ala Phe Ser Ser Trp Phe Tyr Asn Trp Gly Arg Gly Thr
            100                 105                 110

Leu Val Thr Val Ser Ser
            115
```

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Tyr Tyr Ala
            20                  25                  30

Ser Trp Tyr Gln Gln Lys Pro Gly Gln Ala Pro Ile Leu Leu Ile Tyr
            35                  40                  45

Gly Lys Asp Leu Arg Pro Ser Gly Ile Pro Asp Arg Phe Ser Gly Ser
50                  55                  60

Ser Ser Glu Asn Thr Ala Ser Leu Thr Val Thr Gly Ala Gln Ala Glu
65                  70                  75                  80

Asp Glu Gly Glu Tyr Tyr Cys Asn Ser Arg Asp Ser Ser Gly Asn Trp
            85                  90                  95

Val Phe Gly Gly Gly Thr Gln Leu Thr Val Leu
            100                 105
```

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
            35                  40                  45

Gly Trp Ile Gly Thr Tyr Asn Gly Val Thr Asn Tyr Ala Gln Thr Phe
50                  55                  60
```

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Pro Leu Asp Tyr Trp Gly Gln Gly Thr Leu Val
            100                 105                 110

Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Tyr
                85                  90                  95

Thr Phe Gly Gln Gly Thr Lys Val Asp Ile Lys
            100                 105

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Ile Phe Ser Thr Tyr
            20                  25                  30

Ala Met Thr Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Gly Val Phe Asp Tyr Trp Gly Gln Gly Thr Leu Val
            100                 105                 110

Thr Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Glu Tyr Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly His
                85                  90                  95

Asn Asn Pro Tyr Val Phe Gly Thr Gly Thr Lys Val Thr Val Leu
            100                 105                 110

<210> SEQ ID NO 9
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Val Ile Asn Pro Ser Asp Arg Tyr Thr Trp Tyr Ala Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Ile Tyr Tyr Cys
                85                  90                  95

Ala Arg Gly Gly Glu Asp Thr Ala Ser Tyr Tyr Trp Gly Gln Gly Thr
            100                 105                 110

Leu Val Thr Val Ser Ser
        115

<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

```
Ser Ser Glu Leu Thr Gln Asp Pro Ala Val Ser Val Ala Leu Gly Gln
  1               5                  10                  15

Thr Leu Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Thr Ser Gly Asn Thr Asp Ser Leu Thr Ile Thr Gly Ala Gln Ala Glu
 65                  70                  75                  80

Asp Glu Ala Asp Tyr Phe Cys Ser Ser Arg Asp Ser Ser Asp Asn His
                 85                  90                  95

Leu Asn Val Leu Phe Gly Gly Gly Thr Lys Leu Thr Val Leu
            100                 105                 110

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Gly Gly Leu Ile Gln Pro Gly Gly
  1               5                  10                  15

Ser Leu Arg Leu Ser Cys Ala Ala Ser Gly Phe Thr Val Ser Asn Asn
             20                  25                  30

Tyr Met Arg Trp Val Arg Gln Ala Pro Gly Lys Gly Leu Glu Trp Val
         35                  40                  45

Ser Leu Ile Tyr Ser Thr Gly Thr Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Arg Gly Gln Trp Phe Asp Pro Trp Gly Gln Gly Thr Leu Val
            100                 105                 110

Thr Val Ser Ser
        115

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60
```

```
Ser Ser Gly Asn Thr Ala Ser Leu Thr Ile Thr Gly Ala Gln Ala Glu
 65                  70                  75                  80

Asp Glu Ala Asp Tyr Tyr Cys His Ser Arg Asp Ser Asn Gly Asn His
                 85                  90                  95

Val Ile Phe Gly Gly Gly Thr Lys Leu Thr Val Leu
            100                 105

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Asp Ile Val Pro Ile Phe Gly Val Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Asp Arg Gly Ala Phe Asp Ile Trp Gly Gln Gly Thr Met Val
            100                 105                 110

Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Asp Ile Lys
            100                 105

<210> SEQ ID NO 15
<211> LENGTH: 121
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Arg Leu Glu Arg Pro Tyr Tyr Phe Asp Tyr Trp Gly
            100                 105                 110

Gln Gly Thr Leu Val Thr Val Ser Ser
        115                 120

<210> SEQ ID NO 16
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Tyr Glu Leu Thr Gln Pro Pro Ser Leu Ser Val Ala Pro Gly Lys
1               5                   10                  15

Thr Ala Arg Ile Thr Cys Gly Gly Asp Asn Ile Arg Ser Lys Ser Val
            20                  25                  30

Asn Trp Tyr Gln Gln Lys Pro Gly Gln Ala Pro Leu Leu Val Ile Ser
        35                  40                  45

Phe Asp Ser Asp Arg Pro Ser Gly Ile Pro Glu Arg Val Ser Gly Ser
    50                  55                  60

Asn Ser Gly Asn Thr Ala Thr Leu Thr Ile Ser Thr Val Glu Ala Gly
65                  70                  75                  80

Asp Glu Ala Asp Tyr Tyr Cys Gln Val Trp Asp Gly Tyr Val Gly Val
                85                  90                  95

Phe Gly Gly Gly Thr Gln Leu Thr Val Leu
            100                 105

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Gly Tyr
```

```
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Asp Ser Ser Gly Tyr Phe Gly Pro Asp Tyr Trp
            100                 105                 110

Gly Gln Gly Thr Leu Val Thr Val Ser Ser
            115                 120

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
                20                  25                  30

Asn Phe Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Trp Val Phe Gly Thr Gly Thr Lys Val Thr Val Leu
            100                 105                 110

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Thr Asn Phe
                20                  25                  30

Trp Met Asp Trp Val Arg Gln Ala Pro Gly Lys Gly Leu Glu Trp Val
            35                  40                  45

Ala Asp Ile Asn Lys Asp Gly Gly Glu Lys Tyr Tyr Val Asp Ser Val
    50                  55                  60

Lys Gly Arg Phe Thr Ile Ser Arg Asp Asn Ala Gly Asn Ser Leu Tyr
65                  70                  75                  80

Leu Gln Met Asn Ser Leu Arg Ala Glu Asp Thr Ala Val Tyr Tyr Cys
```

```
                    85                  90                  95

Ala Arg Asp Ala Met Arg Gly Gly Asp Leu Asp Tyr Trp Gly Gln Gly
                100                 105                 110

Thr Leu Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Phe Gly Gly Gly Thr Lys Val Asp Ile Lys
            100                 105

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Thr Asn Phe
            20                  25                  30

Trp Met Asp Trp Val Arg Gln Ala Pro Gly Lys Gly Leu Glu Trp Val
        35                  40                  45

Ala Asp Ile Asn Lys Asp Gly Glu Lys Tyr Tyr Val Asp Ser Val
    50                  55                  60

Lys Gly Arg Phe Thr Ile Ser Arg Asp Asn Ala Gly Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Met Arg Gly Gly Asp Leu Asp Tyr Trp Gly Gln Gly
                100                 105                 110

Thr Leu Val Thr Val Ser Ser
        115

<210> SEQ ID NO 22
<211> LENGTH: 106
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 22

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Val Glu Ile Lys
            100                 105

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Pro Glu Trp Met
            35                  40                  45

Gly Val Ile Ser Pro Ser Gly Asp Ala Thr Thr Tyr Ala Pro Lys Phe
50                  55                  60

Gln Gly Arg Leu Thr Met Thr Arg Glu Thr Ser Thr Gly Thr Asp Tyr
65                  70                  75                  80

Met Glu Leu Ser Ser Leu Arg Ser Glu Asp Thr Ala Val Tyr Tyr Cys
                85                  90                  95

Ala Lys Asp Leu Tyr Trp Gly Ala Ala Asp Tyr Trp Gly Gln Gly Thr
            100                 105                 110

Leu Val Thr Val Ser Ser
        115

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ser Val Leu Thr Gln Pro Ala Ser Val Ser Gly Ser Pro Gly Gln
1               5                   10                  15

Ser Ile Thr Ile Ser Cys Thr Gly Thr Ser Gly Asp Val Gly Gly Tyr
                20                  25                  30
```

Asn Tyr Val Ser Trp Tyr Gln His Pro Gly Lys Ala Pro Lys Leu
            35                  40                  45

Met Ile Phe Asp Val Ser Asp Arg Pro Ser Gly Val Ser Ser Arg Phe
 50                  55                  60

Phe Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Lys Leu Thr Val Leu
            100                 105                 110

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Thr Tyr
             20                  25                  30

Ala Met His Trp Val Arg Gln Ala Pro Asp Lys Gly Leu Glu Trp Val
            35                  40                  45

Ala Ile Ile Ser Asp Asp Glu Thr His Lys Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Ile Asn Gly Leu Arg Ala Asp Ser Ala Val Tyr Tyr Cys
                 85                  90                  95

Ala Val His Asp Phe Asp Phe Trp Gly Gln Gly Thr Leu Val Thr Val
            100                 105                 110

Ser Ser

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ser Val Leu Thr Gln Pro Pro Ser Ala Ser Gly Ser Pro Gly Gln
 1               5                  10                  15

Ser Val Thr Ile Ser Cys Thr Gly Thr Asn Ser Asp Ile Gly Gly Tyr
             20                  25                  30

Asn Tyr Val Ser Trp Phe Gln Gln His Pro Gly Lys Ala Pro Lys Leu
            35                  40                  45

Met Ile Tyr Asp Val Asn Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Phe Ala Gly Ser
                 85                  90                  95

Asn Asn Ser Ile Phe Gly Thr Gly Thr Lys Leu Thr Val Leu
            100                 105                 110

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Val Val
                85                  90                  95

Phe Gly Gly Gly Thr Gln Leu Thr Val Leu
            100                 105

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Leu Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Phe
            20                  25                  30

Tyr Trp Thr Trp Ile Arg Gln Pro Pro Gly Lys Ala Leu Glu Trp Ile
        35                  40                  45

Gly Tyr Ile Tyr His Asn Gly Tyr Ser Arg Tyr Ser Pro Ser Leu Lys
50                  55                  60

Ser Arg Val Ser Met Ser Val Asp Thr Ser Arg Asn Gln Phe Ser Leu
65                  70                  75                  80

His Leu Asn Ser Val Thr Ala Ala Asp Thr Ala Val Tyr Tyr Cys Ala
                85                  90                  95

Arg Ala Asn Asn Asp Tyr Leu Phe Phe Asp Leu Trp Gly Arg Gly Thr
            100                 105                 110

Leu Val Thr Val Ser Ser
            115

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Ser Val Val Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Ile Val Ser Trp Tyr Gln His Val Pro Gly Thr Ala Pro Lys Leu Leu
        35                  40                  45

Ile Tyr Gly Asn Ala Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ser Gly Trp Val Leu Gly Gly Gly Thr Lys Val Thr Val Leu
            100                 105                 110

<210> SEQ ID NO 31
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Val Asp Tyr Tyr Asp Ser Ser Gly Tyr Tyr Pro Tyr
                100                 105                 110

Ser Ala Gly Met Asp Val Trp Gly Gln Gly Thr Thr Val Thr Val Ser
        115                 120                 125

Ser

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Ser Pro Ser Thr Leu Ser Ala Ser Val Gly
  1               5                  10                  15

Asp Arg Val Thr Ile Thr Cys Arg Ala Ser Gln Ser Val Asp Thr Trp
                 20                  25                  30

Leu Ala Trp Tyr Gln Gln Pro Gly Lys Ala Pro Arg Leu Leu Ile
         35                  40                  45

Ser Lys Ala Ser Arg Leu Gln Thr Asp Ile Pro Ser Arg Phe Ser Ala
 50                  55                  60

Gly Gly Ser Gly Thr Val Phe Thr Leu Thr Ile Ser Ser Leu Gln Pro
 65                  70                  75                  80

Asp Asp Phe Ala Thr Tyr Tyr Cys Gln Gln Tyr Tyr Ser Phe Pro Thr
                 85                  90                  95

Phe Gly Gln Gly Thr Lys Leu Glu Ile Lys
                100                 105

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Tyr Met Asn Trp Ile Arg Gln Ala Pro Gly Lys Gly Leu Glu Trp Val
         35                  40                  45

Ser Tyr Ile Ser Ser Gly Gly Thr Thr Ile Tyr Tyr Ala Asp Ser Val
 50                  55                  60

Lys Gly Arg Phe Thr Ile Ser Arg Asp Asn Ala Lys Thr Ser Leu Phe
 65                  70                  75                  80

Leu Gln Met Asp Ser Leu Ala Ile Glu Asp Thr Ala Val Tyr Tyr Cys
                 85                  90                  95

Val Arg Asp Phe Asn Ser Gly Ser Ala Phe Asp Leu Trp Gly Gln Gly
                100                 105                 110
```

Thr Met Val Thr Val Ser Ser
        115

<210> SEQ ID NO 34
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Pro Val Leu Thr Gln Ser Pro Ser Val Ser Val Ser Pro Gly Gln
1               5                   10                  15

Thr Gly Thr Ile Thr Cys Ser Gly Asp Lys Leu Gly Asp Lys Tyr Val
            20                  25                  30

Ala Trp Tyr Gln Gln Lys Ser Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Pro Val
65                  70                  75                  80

Asp Glu Ala Asp Tyr Tyr Cys Gln Ala Trp Asp Ser Ser Thr Val Phe
                85                  90                  95

Gly Gly Gly Thr Lys Leu Thr Val Leu
            100                 105

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Phe Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Asn Thr Val Arg Ser Asp Tyr Trp Gly Gln Gly Thr Leu
            100                 105                 110

Val Thr Val Ser Ser
        115

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 36

Gln Ala Val Val Thr Gln Pro Pro Ser Ala Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Thr Thr Arg Trp Val Phe Gly Thr Gly Thr Lys Leu Thr Val Leu
            100                 105                 110

<210> SEQ ID NO 37
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Met Gln Leu Val Gln Ser Gly Ala Glu Val Lys Lys Pro Gly Ala
1               5                   10                  15

Ser Val Lys Val Ser Cys Lys Ala Ser Glu His Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asp Asp Tyr Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Asn Gly Gly Asn Ser Val Phe Gly Ala Leu Asp Ile
            100                 105                 110

Trp Gly Gln Gly Thr Met Val Thr Val Ser Ser
        115                 120

<210> SEQ ID NO 38
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Ser Glu Leu Thr Gln Asp Pro Ala Val Ser Val Ala Ser Gly Gln
1               5                   10                  15

Thr Val Arg Ile Thr Cys Gln Gly Asp Ser Leu Arg Arg Tyr Tyr Ala
            20                  25                  30

Gly Trp Tyr Gln Gln Lys Pro Gly Gln Ala Pro Val Leu Val Ile Phe
        35                  40                  45
```

```
Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Tyr Val Phe Gly Thr Gly Thr Lys Val Thr Val Leu
                100                 105
```

<210> SEQ ID NO 39
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Thr Gly Leu Gly Gly Trp Leu Arg Ile Asp Asp Ala Phe Asp Ile
                100                 105                 110

Trp Gly Gln Gly Thr Met Val Thr Val Ser Ser
            115                 120
```

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Gln Val Phe Gly Gly Gly Thr Lys Leu Thr Val Leu
                100                 105
```

<210> SEQ ID NO 41
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Leu His Trp Val Arg Gln Ala Pro Gly Gln Gly Leu Glu Trp Met
        35                  40                  45

Gly Met Val Asn Pro Ile Gly Tyr Thr Asn Tyr Ser Gln Thr Phe
    50                  55                  60

Gln Gly Arg Val Thr Val Thr Arg Asp Thr Ala Thr Ser Thr Ala Tyr
65                  70                  75                  80

Met Glu Leu Asn Ser Leu Arg Ser Glu Asp Thr Ala Val Tyr Phe Cys
                85                  90                  95

Ala Arg Gly Phe Gly Phe Ile Asp His Trp Gly Gln Gly Thr Leu Val
            100                 105                 110

Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Leu Leu Val Leu Thr Gln Ser Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Ala
65                  70                  75                  80

Asp Glu Ala Asp Tyr Tyr Cys Gln Ser Ala Asp Ser Ser Asp Ile Val
                85                  90                  95

Val Phe Gly Gly Gly Thr Gln Leu Thr Val Leu
            100                 105

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Gly Gly Leu Val Gln Pro Gly Arg

```
                1               5                   10                  15
            Ser Leu Arg Leu Ser Cys Ala Ala Ser Gly Phe Thr Phe Asp Asp Tyr
                            20                  25                  30

Ala Met His Trp Val Arg Gln Ala Pro Gly Lys Gly Leu Glu Trp Val
                        35                  40                  45

Ser Gly Ile Ser Trp Asn Ser Gly Ser Ile Gly Tyr Ala Asp Ser Val
                    50                  55                  60

Lys Gly Arg Phe Thr Ile Ser Arg Asp Asn Ala Lys Asn Ser Leu Tyr
            65                  70                  75                  80

Leu Gln Met Asn Ser Leu Arg Ala Glu Asp Thr Ala Leu Tyr Tyr Cys
                            85                  90                  95

Ala Lys Asp Ile Lys Val Ala Arg Gly Tyr Gly Met Asp Phe Trp Gly
                        100                 105                 110

Gln Gly Thr Met Val Thr Val Ser Ser
                        115                 120

<210> SEQ ID NO 44
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Pro Val Leu Thr Gln Pro Pro Ser Val Ser Ala Ala Pro Gly Gln
1               5                   10                  15

Met Val Thr Ile Ser Cys Ser Gly Ser Ser Ser Asn Ile Gly Asp Asn
                20                  25                  30

Tyr Val Ser Trp Tyr Gln Gln Phe Pro Gly Thr Ala Pro Lys Leu Leu
            35                  40                  45

Ile Tyr Gly Asp Asn Arg Arg Pro Ser Ala Val Pro Asp Arg Phe Ser
        50                  55                  60

Gly Ser Asn Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Ser Leu
                85                  90                  95

Ser Gly Trp Val Phe Gly Gly Gly Thr Lys Leu Thr Val Leu
            100                 105                 110

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Asn Val Ser Thr Asn
                20                  25                  30

Ile Ser Ser Trp Asn Trp Ile Arg Gln Ser Pro Ser Arg Gly Leu Glu
            35                  40                  45

Trp Leu Gly Arg Thr Tyr Tyr Arg Ser Lys Trp Phe Asn Asp Tyr Ala
        50                  55                  60

Val Ser Val Lys Ser Arg Ile Thr Ile Asn Pro Asp Thr Ser Lys Asn
```

```
                65                  70                  75                  80
Leu Phe Ser Leu Gln Leu Asn Ser Val Thr Pro Glu Asp Thr Ala Val
                    85                  90                  95

Tyr Tyr Cys Ala Arg Gly Ser Ala Phe Asn Ile Trp Gly Gln Gly Thr
                100                 105                 110

Met Val Thr Val Ser Ser
        115

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser Tyr Val Leu Thr Gln Pro Ala Ser Val Ser Gly Ser Pro Gly Gln
1               5                   10                  15

Ser Ile Thr Ile Ser Cys Ile Gly Thr Ser Ser Asp Val Gly Asn Ser
                20                  25                  30

Asn Leu Val Ser Trp Tyr Gln His His Pro Gly Lys Ala Pro Lys Leu
            35                  40                  45

Met Ile Phe Glu Val Thr Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Val Thr Val Leu
                100                 105                 110

<210> SEQ ID NO 47
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Asn Trp Ile Arg Gln Ala Pro Gly Lys Gly Leu Glu Trp Leu
            35                  40                  45

Ser Tyr Ile Ser Ser Gly Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Gly Gly Asn Ser Val Leu Phe Asp Tyr Trp Gly
                100                 105                 110

Gln Gly Thr Leu Val Thr Val Ser Ser
            115                 120
```

```
<210> SEQ ID NO 48
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Arg Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Ala Asn His
                85                  90                  95

Phe Tyr Val Phe Gly Thr Gly Thr Lys Val Thr Val Leu
            100                 105

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Ser His
            20                  25                  30

Tyr Ile His Trp Val Arg Gln Ala Pro Gly Gln Gly Leu Gln Trp Met
        35                  40                  45

Gly Ile Ile Asn Ala Asn Gly Gly Ser Thr Thr Tyr Ala Gln Glu Phe
    50                  55                  60

Leu Gly Arg Val Ile Met Thr Thr Asp Thr Ser Thr Gly Thr Ala Tyr
65                  70                  75                  80

Leu Glu Leu Ile Ser Leu Arg Ser Asp Asp Thr Ala Val Tyr Tyr Cys
                85                  90                  95

Ala Arg Asp Met Ala Gly Thr Trp Asn His Gly Ser Ile Asp Ser Trp
            100                 105                 110

Gly Gln Gly Thr Leu Val Thr Val Ser Ser
        115                 120

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Pro Val Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
               100                 105                 110

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu Tyr Trp Val Arg Gln Ala Pro Gly Gln Gly Leu Glu Trp Met
        35                  40                  45

Gly Trp Ile Asp Pro Asn Ser Gly Gly Thr Asn Tyr Ala Gln Lys Phe
 50                  55                  60

Gln Gly Arg Val Thr Val Thr Arg Asp Thr Ser Ile Ser Thr Ala Tyr
 65                  70                  75                  80

Met Glu Leu Thr Arg Leu Arg Ser Asp Asp Thr Ala Val Tyr Phe Cys
                85                  90                  95

Ala Ile Gly Tyr Tyr Gly Ser Thr Tyr Phe Asp Tyr Trp Gly Gln Gly
               100                 105                 110

Thr Leu Val Thr Val Ser Ser Gly
        115                 120

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Val Leu Thr Gln Pro Pro Ser Ala Ser Ala Thr Pro Gly Gln
1               5                   10                  15

Arg Val Thr Ile Ser Cys Ser Gly Ser Thr Ser Asn Ile Gly Thr Asn
            20                  25                  30

Ala Val Asp Trp Tyr Gln Gln Phe Pro Gly Thr Ala Pro Lys Leu Leu
        35                  40                  45

Ile Phe Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80
```

-continued

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 53
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Met Asp Pro Ser Gly Gly Ser Ala Thr Tyr Ala Gln Lys Leu
    50                  55                  60

Gln Gly Arg Ile Ile Met Thr Arg Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Asp Pro Asp Phe Tyr Gly Leu Gly Ser Tyr Ser His Gly Ala
            100                 105                 110

Phe Asp Ile Trp Gly Gln Gly Thr Met Val Thr Val Ser Ser
        115                 120                 125

<210> SEQ ID NO 54
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Pro Val Leu Thr Gln Pro Ala Ser Val Ser Gly Ser Pro Gly Gln
1               5                   10                  15

Ser Val Thr Ile Ser Cys Thr Gly Ala Gly Ser Asp Val Gly Gly Tyr
            20                  25                  30

Asp Tyr Val Ser Trp Tyr Gln Gln His Pro Gly Lys Ala Pro Lys Leu
        35                  40                  45

Ile Ile Phe Asp Val Asn Asn Arg Pro Ser Gly Val Ser Tyr Arg Phe
    50                  55                  60

Ser Gly Ser Lys Ser Ala Asn Thr Ala Ser Leu Thr Ile Ser Gly Leu
65                  70                  75                  80

Gln Ser Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Asn Tyr
            20                  25                  30

Phe Ile Ala Trp Val Arg Gln Met Pro Gly Lys Gly Leu Glu Trp Met
        35                  40                  45

Gly Met Phe Tyr Pro Gly Asp Ser Lys Thr Thr Tyr Asn Pro Ser Phe
    50                  55                  60

Gln Gly Gln Val Ile Ile Ser Ala Asp Lys Ser Ile Asn Thr Ala Tyr
65                  70                  75                  80

Leu Gln Trp Ser Ser Leu Lys Ala Ser Asp Thr Ala Val Tyr Tyr Cys
                85                  90                  95

Ala Arg Ala Phe Tyr Ala Ala Gly Asn Tyr Phe Asp Tyr Trp Gly Gln
            100                 105                 110

Gly Thr Leu Val Thr Val Ser Ser Gly
        115                 120

<210> SEQ ID NO 56
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Tyr Tyr Ala
            20                  25                  30

Ser Trp Tyr Gln Gln Lys Pro Gly Gln Ala Pro Arg Leu Leu Met Tyr
        35                  40                  45

Gly Lys Asn Ile Arg Pro Ser Gly Ile Pro Asp Arg Phe Ser Gly Thr
    50                  55                  60

Asp Ser Gly Asn Thr Ala Phe Leu Thr Ile Thr Gly Ala Gln Ala Glu
65                  70                  75                  80

Asp Glu Ala Asp Tyr Tyr Cys Asn Ser Arg Asp Thr Asn Ala Asn Gln
                85                  90                  95

Pro Leu Val Leu Phe Gly Gly Gly Thr Lys Val Thr Val Leu
            100                 105                 110

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Ser Asn Tyr Tyr Gly Ser Gly Ser Ser Phe Asp Tyr Trp Gly Gln
                100                 105                 110

Gly Thr Leu Val Thr Val Ser Ser
            115                 120

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Pro Val Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
             20                  25                  30

Asn Phe Val Ser Trp Tyr Gln Gln His Pro Gly Lys Ala Pro Lys Leu
         35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Thr Ser Ser
                 85                  90                  95

Ser Thr Arg Tyr Val Phe Gly Thr Gly Thr Lys Leu Thr Val Leu
                100                 105                 110

<210> SEQ ID NO 59
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Asp Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Val Gly Glu Leu Trp Gly Trp Gly Gln Gly Thr Leu Val
            100                 105                 110

Thr Val Ser Ser
        115

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Val Leu Thr Gln Pro Ala Ser Val Ser Gly Tyr Pro Gly Gln
1               5                   10                  15

Ser Ile Thr Ile Ser Cys Ile Gly Ser Ser Ser Asp Val Gly Phe Ser
            20                  25                  30

Gln Tyr Val Ser Trp Tyr Gln His Pro Asp Arg Pro Pro Lys Leu
        35                  40                  45

Ile Ile Tyr Asp Val Ser Asn Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                85                  90                  95

Gly Thr Tyr Val Phe Gly Thr Gly Thr Lys Val Thr Val Leu
            100                 105                 110

<210> SEQ ID NO 61
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Phe Gly Gly Thr Thr Glu Tyr Ala Ala
50                  55                  60

Ser Val Lys Gly Arg Phe Ser Ile Ser Arg Asp Asp Ser Lys Asn Ile
65                  70                  75                  80

Ala Tyr Val Gln Met Asn Ser Leu Lys Thr Asp Asp Thr Ala Val Tyr
                85                  90                  95

Tyr Cys Thr Arg Asp Ser Gly Pro Gly Trp Glu Arg Ser Phe Asp Tyr
            100                 105                 110

Trp Gly Gln Gly Thr Leu Val Thr Val Ser Ser
        115                 120

<210> SEQ ID NO 62
<211> LENGTH: 108
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 62

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Gln Leu Thr Val Leu
            100                 105

<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ile Val Gly Ser Thr Asp Tyr Trp Gly Gln Gly Thr Leu
            100                 105                 110

Val Thr Val Ser Ser
        115

<210> SEQ ID NO 64
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ala Val Leu Thr Gln Pro Ala Ser Val Ser Gly Ser Pro Gly Gln
1               5                   10                  15

Ser Ile Thr Ile Ser Cys Thr Gly Thr Asn Ser Asp Ile Gly Thr Tyr
            20                  25                  30

Asn Tyr Val Ser Trp Tyr Gln Gln His Pro Gly Lys Ala Pro Lys Leu

```
                35                  40                  45
Ile Ile Tyr Asp Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Trp Val Phe Gly Gly Gly Thr Gln Leu Thr Val Leu
            100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
             35                  40                  45

Gly Trp Ile Asp Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Lys Asp Asp Tyr Trp Gly Gln Gly Thr Leu Val Thr Val Ser Ser
            100                 105                 110
```

<210> SEQ ID NO 66
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gln Ala Gly Leu Thr Gln Pro Ala Ser Val Ser Gly Ser Pro Gly Gln
 1               5                  10                  15

Ser Ile Ala Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
             35                  40                  45

Met Ile Tyr Glu Val Ile Lys Arg Pro Ser Gly Ile Ser Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Phe Ser Tyr Thr Ser Ser
                 85                  90                  95

Thr Thr Arg Tyr Val Phe Gly Thr Gly Thr Lys Val Thr Val Leu
            100                 105                 110
```

```
<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Val Ile Asn Pro Ser Asp Arg Tyr Thr Tyr Ala Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Ile Tyr Tyr Cys
                85                  90                  95

Ala Arg Gly Gly Glu Asp Thr Ala Ser Tyr Tyr Trp Gly Gln Gly Thr
            100                 105                 110

Leu Val Thr Val Ser Ser
        115

<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ser Ser Glu Leu Thr Gln Asp Pro Ala Val Ser Val Ala Leu Gly Gln
1               5                   10                  15

Thr Leu Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Thr Asp Ser Leu Thr Ile Thr Gly Ala Gln Ala Glu
65                  70                  75                  80

Asp Glu Ala Asp Tyr Phe Cys Ser Ser Arg Asp Ser Ser Asp Asn His
                85                  90                  95

Leu Asn Val Leu Phe Gly Gly Gly Thr Lys Val Thr Val Leu
            100                 105                 110

<210> SEQ ID NO 69
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Thr Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Glu Tyr Ser Ser Gly Trp Ala Gly Asp Tyr Trp Gly Gln
            100                 105                 110

Gly Thr Leu Val Thr Val Ser Ser
            115                 120

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ser Val Leu Thr Gln Pro Pro Ser Val Ser Gly Ser Pro Gly Gln
 1               5                  10                  15

Ser Ile Thr Ile Ser Cys Thr Gly Thr Ser Arg Asp Val Gly Leu Tyr
            20                  25                  30

Asn Tyr Val Ser Trp Tyr Gln Gln His Pro Asp Lys Ala Pro Lys Leu
        35                  40                  45

Leu Ile Tyr Asp Val Ser Glu Arg Pro Ser Gly Ile Ser Asn Arg Phe
 50                  55                  60

Ser Gly Ser Lys Ser Gly Asn Thr Ala Thr Leu Thr Ile Ser Gly Leu
 65                  70                  75                  80

Gln Pro Glu Asp Glu Ala Asp Tyr Tyr Cys Gly Ser Tyr Thr Ser Ser
                 85                  90                  95

Ser Thr Arg Tyr Val Phe Gly Thr Gly Thr Lys Val Thr Val Leu
            100                 105                 110

<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80
```

Met Glu Leu Ser Arg Leu Arg Ser Asp Asp Thr Ala Val Tyr Tyr Cys
            85                  90                  95

Ala Arg Glu Gly Val Gly Ala Thr Ser Trp Phe Asp Pro Trp Gly Gln
        100                 105                 110

Gly Thr Leu Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Tyr His Ala
            20                  25                  30

Ser Trp Tyr Gln Gln Lys Pro Gly Gln Ala Pro Val Leu Val Ile Tyr
        35                  40                  45

Asn Lys Asn Asn Arg Pro Ser Gly Ile Pro Asp Arg Phe Ser Gly Ser
    50                  55                  60

Ser Ser Gly Asn Thr Asp Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Tyr
                85                  90                  95

Val Phe Gly Thr Gly Thr Lys Leu Thr Val Leu
            100                 105

<210> SEQ ID NO 73
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ala Met Ser His Asp Gly Ile Gln Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Gly Gly Gly Phe Ala Tyr Gly Met Glu Asp Tyr Trp Gly Gln
            100                 105                 110

Gly Thr Leu Val Thr Val Ser Ser
        115                 120

<210> SEQ ID NO 74

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ala Ile Gln Met Thr Gln Ser Pro Ser Ser Leu Ser Ala Ser Val Gly
1               5                   10                  15

Asp Arg Val Ser Phe Thr Cys Gln Ala Ser Gln Asp Ile Ser Asn Tyr
            20                  25                  30

Leu Asn Trp Tyr Gln Gln Lys Pro Gly Lys Ala Pro Lys Leu Met Ile
        35                  40                  45

Ser Asp Ala Ser Thr Leu Glu Thr Gly Val Pro Ser Arg Phe Ser Gly
50                  55                  60

Ser Gly Ser Gly Thr Tyr Phe Thr Phe Thr Ile Ser Ser Leu Gln Pro
65                  70                  75                  80

Asp Asp Phe Ala Thr Tyr Tyr Cys Gln His Tyr Asp Ser Phe Pro Leu
            85                  90                  95

Thr Phe Gly Gly Gly Thr Lys Val Glu Ile Lys
            100                 105

<210> SEQ ID NO 75
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Ala Glu Glu Lys Thr Pro Gly Ala
1               5                   10                  15

Ser Val Lys Ile Ser Cys Lys Ala Ser Gly Asn Thr Phe Asn Asn Tyr
            20                  25                  30

Asp Ile His Trp Val Arg Gln Ala Pro Gly Glu Arg Pro Glu Trp Met
        35                  40                  45

Gly Trp Ile Asn Ser Gly Asn Gly Asp Thr Arg Asn Ser Gln Lys Phe
50                  55                  60

Gln Gly Arg Val Thr Ile Thr Trp Asp Thr Ser Ala Ser Thr Ala Tyr
65                  70                  75                  80

Met Glu Leu Ser Ser Leu Thr Ser Glu Asp Thr Gly Val Tyr Phe Cys
            85                  90                  95

Ala Arg Ala Glu Gly Pro Leu Asp Tyr Trp Gly Gln Gly Thr Leu Val
            100                 105                 110

Thr Val Ser Ser
        115

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Thr Pro Ser Ser Leu Ser Ala Ser Val Gly
1               5                   10                  15
```

```
Asp Arg Val Thr Ile Thr Cys Arg Ala Ser Gln Gly Ile Tyr Asn Tyr
                20                  25                  30

Leu Ala Trp Tyr Gln Gln Lys Leu Gly Lys Ala Pro Asn Leu Leu Ile
        35                  40                  45

Tyr Ala Thr Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
                100                 105

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Lys
                20                  25                  30

Trp Met His Trp Val Arg Gln Ala Pro Gly Gln Gly Pro Glu Trp Met
            35                  40                  45

Gly Val Ile Asn Pro Ser Ser Gly Gly Thr Thr Tyr Ala Gln Lys Phe
 50                  55                  60

Gln Gly Arg Leu Thr Val Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Asp Asp Val Phe Asp Tyr Tyr Phe Gly Leu Asp Val Trp Gly
                100                 105                 110

Gln Gly Thr Thr Val Thr Val Ser Ser
            115                 120

<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Tyr Tyr Ala
                20                  25                  30

Ser Trp Tyr Gln Gln Lys Pro Gly Gln Ala Pro Arg Leu Leu Ile Tyr
            35                  40                  45

Gly Lys Asn Ile Arg Pro Ser Gly Ile Pro Asp Arg Phe Ser Gly Thr
 50                  55                  60

Asp Ser Gly Asn Thr Asp Phe Leu Thr Ile Thr Gly Ala Gln Ala Glu
 65                  70                  75                  80
```

```
Asp Glu Ala Asp Tyr Tyr Cys Asn Ser Arg Asp Thr Asp Ala Asn Gln
                85                  90                  95

Pro Leu Val Leu Phe Gly Gly Gly Thr Lys Leu Thr Val Leu
            100                 105                 110

<210> SEQ ID NO 79
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Gly Asp Leu Val Gln Pro Gly Gly
1               5                   10                  15

Ser Leu Arg Leu Ser Cys Ala Ala Ser Gly Phe Leu Phe Ser Asn Ser
            20                  25                  30

Trp Met Thr Trp Val Arg Gln Ala Pro Gly Lys Gly Leu Glu Trp Leu
        35                  40                  45

Ala Asn Ile Lys Pro Asp Gly Ser Gly Gln Tyr Tyr Val Asp Ser Leu
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Met Tyr Tyr Cys
                85                  90                  95

Ala Arg Asp Arg Gly Asn Asp Gly Leu Asp Tyr Trp Gly Gln Gly Thr
            100                 105                 110

Leu Val Thr Val Ser Ser
        115

<210> SEQ ID NO 80
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ser Tyr Glu Leu Thr Gln Pro Pro Ser Val Ser Val Ser Pro Gly Gln
1               5                   10                  15

Thr Ala Arg Ile Thr Cys Ser Gly Glu Lys Leu Asp Asp Lys Tyr Thr
            20                  25                  30

Phe Trp Tyr Gln Gln Arg Thr Gly Gln Thr Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Val
65                  70                  75                  80

Asp Glu Ala Asp Tyr Tyr Cys Gln Thr Tyr Asp Ser Gly Ala Pro Val
                85                  90                  95

Phe Gly Gly Gly Thr Lys Leu Thr Val Leu
            100                 105

<210> SEQ ID NO 81
<211> LENGTH: 117
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 81

Glu Val Gln Leu Val Glu Ser Gly Ala Glu Leu Lys Lys Pro Gly Ala
1               5                   10                  15

Ser Val Lys Val Ser Cys Met Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Ser Thr Tyr Thr Asp Tyr Trp Gly Gln Gly Thr Leu
            100                 105                 110

Val Thr Val Ser Ser
        115

<210> SEQ ID NO 82
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asp Phe Val Ala Trp Tyr Gln Gln His Pro Gly Lys Ala Pro Lys Leu
        35                  40                  45

Leu Ile Tyr Asp Val Ser Asn Arg Pro Ser Gly Val Ser Asn Arg Phe
    50                  55                  60

Ser Gly Ser Lys Ser Gly Asn Thr Ala Ser Leu Lys Ile Ser Gly Leu
65                  70                  75                  80

Arg Ala Glu Asp Glu Ala Asp Tyr Tyr Cys Ser Ser Tyr Thr Ser Ser
                85                  90                  95

Ser Ala Arg Trp Val Phe Gly Gly Gly Thr Lys Val Thr Val Leu
            100                 105                 110

<210> SEQ ID NO 83
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val

```
                35                  40                  45
Gly Phe Ile Arg Ser Lys Ala Phe Gly Gly Thr Thr Glu Tyr Ala Ala
        50                  55                  60

Ser Val Lys Gly Arg Phe Thr Ile Ser Arg Asp Asp Ser Asn Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Ser Gly Pro Gly Trp Glu Arg Ser Phe Asp Tyr
                100                 105                 110

Trp Gly Gln Gly Thr Leu Val Thr Val Ser Ser
        115                 120
```

<210> SEQ ID NO 84
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Lys Leu Thr Val Leu
                100                 105
```

<210> SEQ ID NO 85
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Gln Val Gln Leu Val Gln Ser Gly Ala Glu Glu Lys Thr Pro Gly Ala
1               5                   10                  15

Ser Val Lys Ile Ser Cys Lys Ala Ser Gly Asn Thr Phe Asn Asn Tyr
                20                  25                  30

Asp Ile His Trp Val Arg Gln Ala Pro Gly Glu Arg Pro Glu Trp Met
            35                  40                  45

Gly Trp Ile Asn Ser Gly Asn Gly Asp Thr Arg Asn Ser Gln Lys Phe
        50                  55                  60

Gln Gly Arg Val Thr Ile Thr Trp Asp Thr Ser Ala Ser Thr Ala Tyr
65                  70                  75                  80

Met Glu Leu Ser Ser Leu Thr Ser Glu Asp Thr Gly Val Tyr Phe Cys
                85                  90                  95

Ala Arg Ala Glu Gly Pro Leu Asp Tyr Trp Gly Gln Gly Thr Leu Val
```

```
                  100                 105                 110

Thr Val Ser Ser
        115

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Tyr
            20                  25                  30

Leu Ala Trp Tyr Gln Gln Lys Leu Gly Lys Ala Pro Asn Leu Leu Ile
        35                  40                  45

Tyr Ala Thr Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 87
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ser Pro Glu Trp Met
        35                  40                  45

Gly Trp Ile Asn Val Gly Asn Gly Asn Ile Arg Tyr Ser Gln Lys Phe
    50                  55                  60

Gln Gly Arg Val Thr Phe Thr Gly Asp Thr Ser Ala Thr Thr Ala Tyr
65                  70                  75                  80

Met Asp Leu Ser Ser Leu Arg Ser Glu Asp Thr Ala Val Phe Tyr Cys
                85                  90                  95

Ala Arg Glu Gly Ala Ala Ser Gly Leu Asp Leu Asp Tyr Trp Gly Gln
            100                 105                 110

Gly Thr Leu Val Thr Val Ser Ser
        115                 120

<210> SEQ ID NO 88
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 88

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys His Val
            20                  25                  30

His Trp Tyr Gln Gln Lys Pro Gly Gln Ala Pro Val Leu Val Ile Asn
        35                  40                  45

Tyr Asp Ser Asp Arg Pro Ser Gly Ile Pro Glu Arg Leu Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Thr Ser Asp His
                85                  90                  95

Val Ile Phe Gly Gly Gly Thr Lys Leu Thr Val Leu
            100                 105

<210> SEQ ID NO 89
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Leu Asp Gly Ser Asn Arg His Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Met Tyr Tyr Cys
                85                  90                  95

Ala Gln Asp Leu Tyr Asp Asp Asn Arg Trp Gly Val Phe Asp Tyr Trp
            100                 105                 110

Gly Gln Gly Thr Leu Val Thr Val Ser Ser
        115                 120

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
            100                 105

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Leu Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Pro Gly Ala Gly Gly Tyr Phe Asp Tyr Trp Gly Gln Gly
                100                 105                 110

Thr Leu Val Thr Val Ser Ser
        115

<210> SEQ ID NO 92
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ser Tyr Val Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Pro Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Tyr Val Phe Gly Thr Gly Thr Lys Leu Thr Val Leu
                100                 105                 110

```
<210> SEQ ID NO 93
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Met Lys Lys Pro Gly Ser
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Ser Gln Trp Tyr Gln Leu Tyr Gly Ala Asp Tyr Tyr
            100                 105                 110

Tyr Gly Met Asp Val Trp Gly Gln Gly Thr Thr Val Thr Val Ser Ser
        115                 120                 125

<210> SEQ ID NO 94
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ser Ala Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
            100                 105                 110

<210> SEQ ID NO 95
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95
```

```
Glu Val Gln Leu Val Gln Ser Gly Ala Glu Val Thr Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asn Ala Gly Leu Gly Asp Tyr Trp Gly Gln Gly Thr Leu
                100                 105                 110

Val Thr Val Ser Ser
            115
```

<210> SEQ ID NO 96
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Gln Ala Gly Leu Thr Gln Pro Ala Ser Val Ser Val Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Ile
                85                  90                  95

Asn Ser Arg Tyr Val Phe Gly Thr Gly Thr Lys Val Thr Val Leu
                100                 105                 110
```

<210> SEQ ID NO 97
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Gly Thr Pro Ser Leu Lys Tyr Asp Tyr Tyr Tyr Gly Met Asp
            100                 105                 110

Val Trp Gly Gln Gly Thr Thr Val Thr Val Ser Ser
            115                 120
```

<210> SEQ ID NO 98
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln Tyr Pro Gly Lys Ala Pro Lys Leu
             35                  40                  45

Met Ile Tyr Asp Val Ser Lys Arg Pro Ser Gly Val Ser His Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Gly Gly Thr Lys Leu Thr Val Leu
            100                 105                 110
```

<210> SEQ ID NO 99
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Met
             35                  40                  45

Gly Ile Ile Asn Pro Ser Gly Gly Tyr Thr Ser Ser Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Arg Asp Ser Gly Ser Tyr Tyr Asp Ala Phe Asp Ile Trp
            100                 105                 110

Gly Gln Gly Thr Met Val Thr Val Ser Ser
            115                 120
```

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
        35                  40                  45

Gly Lys Asn Asn Arg Pro Ala Gly Ile Ser Asp Arg Phe Ser Gly Ser
50                  55                  60

Asp Ser Glu Asp Ile Ala Ser Leu Thr Ile Thr Gly Ala Gln Ala Glu
65                  70                  75                  80

Asp Glu Ala Asp Tyr Tyr Cys Asn Ser Arg Asp Ser Asn Ala His Trp
                85                  90                  95

Val Phe Gly Gly Gly Thr Lys Leu Thr Val Leu
            100                 105

<210> SEQ ID NO 101
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Gly Ile Ser Gly Ser Gly Asp Ser Ala Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu His Met Asn Ser Leu Thr Ala Glu Asp Thr Ala Val Tyr Tyr Cys
                85                  90                  95

Ala Ser Gly Gly Asn Tyr Gly Ser Gly Thr Ile Val Ser His Gly Met
            100                 105                 110

Asp Val Trp Gly Gln Gly Thr Thr Val Thr Val Ser Ser
        115                 120                 125

<210> SEQ ID NO 102
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ser Val Val Thr Gln Pro Pro Ser Val Ser Ala Ala Pro Gly His

```
            1               5                  10                 15
Lys Val Thr Ile Ser Cys Ser Gly Asn Ser Ser Asn Val Gly Arg Asn
            20                 25                 30

Tyr Val Ser Trp Tyr Gln Gln Val Pro Gly Thr Ala Pro Lys Leu Leu
            35                 40                 45

Ile Tyr Asp Asp Asn Lys Arg Pro Ser Gly Ile Pro Asp Arg Phe Ser
50                 55                 60

Gly Ser Thr Ser Gly Ala Ser Ala Thr Leu Val Ile Thr Gly Leu Gln
65                 70                 75                 80

Thr Gly Asp Glu Ala Asp Tyr Tyr Cys Gly Ala Trp Asp Ser Ser Leu
                85                 90                 95

Ser Ala Gly Val Phe Gly Gly Gly Thr Lys Leu Thr Val Leu
                100                105                110

<210> SEQ ID NO 103
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Asn Asn Tyr
            20                 25                 30

Ala Met Ser Trp Val Arg Gln Ala Pro Gly Lys Gly Leu Glu Trp Val
            35                 40                 45

Ser Thr Ile Ser Gly Ser Gly Glu Asn Thr His Tyr Ala Asp Ser Val
50                 55                 60

Lys Gly Arg Phe Thr Ile Ser Arg Asp Asn Ser Lys Asp Thr Leu Tyr
65                 70                 75                 80

Leu Gln Met Ser Ser Leu Arg Ala Glu Asp Thr Ala Val Tyr Tyr Cys
                85                 90                 95

Ala Asn Gln Tyr Asp Thr Thr Asp Tyr Tyr Trp Gly Glu Tyr Phe
                100                105                110

His His Trp Gly Gln Gly Thr Leu Val Thr Val Ser Ser
        115                120                125

<210> SEQ ID NO 104
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ser Tyr Glu Leu Thr Gln Pro Pro Ser Val Ser Val Ser Pro Gly Gln
1               5                  10                 15

Thr Ala Arg Ile Thr Cys Ser Gly Asp Ala Leu Pro Lys Gln Tyr Ala
            20                 25                 30

Tyr Trp Tyr Gln Gln Lys Pro Gly Gln Ala Pro Val Leu Val Ile Tyr
            35                 40                 45

Lys Asp Ser Glu Arg Pro Ser Gly Ile Pro Glu Arg Phe Ser Gly Ser
50                 55                 60

Ser Ser Gly Thr Thr Val Thr Leu Thr Ile Ser Gly Val Gln Ala Glu
```

```
                65                  70                  75                  80
Asp Glu Ala Asp Tyr Tyr Cys Gln Ser Ala Asp Ser Ser Gly Thr Tyr
                    85                  90                  95

Val Val Phe Gly Gly Gly Thr Lys Leu Thr Val Leu
            100                 105
```

```
<210> SEQ ID NO 105
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Arg Ala Phe Asp Ile Trp Gly Gln Gly Thr Met Val
            100                 105                 110

Thr Val Ser Ser
        115
```

```
<210> SEQ ID NO 106
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Phe Val Ser Trp Tyr Gln Gln His Pro Gly Lys Ala Pro Lys Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Trp Val Phe Gly Gly Gly Thr Lys Leu Thr Val Leu
            100                 105                 110
```

```
<210> SEQ ID NO 107
<211> LENGTH: 118
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Gln Ser Gly Val Glu Val Lys Lys Pro Gly Ala
1               5                   10                  15

Ser Val Lys Val Ser Cys Lys Val Ser Gly Asn Thr Leu Thr Glu Ile
            20                  25                  30

Ser Met His Trp Val Arg Gln Val Pro Gly Lys Gly Leu Glu Trp Met
        35                  40                  45

Gly Gly Phe Asp Leu Glu Asp Gly Glu Thr Val Tyr Ala Gln Lys Phe
    50                  55                  60

Gln Gly Arg Val Thr Leu Thr Glu Asp Thr Ser Ile Asp Thr Ala Tyr
65                  70                  75                  80

Glu Leu Arg Ser Leu Arg Ser Glu Asp Thr Ala Val Tyr Tyr Cys Ala
                85                  90                  95

Thr Gly Pro Ala Gly Tyr Arg Leu Phe Glu Tyr Trp Gly Gln Gly Thr
            100                 105                 110

Leu Val Thr Val Ser Ser
        115

<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Leu Pro Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu
            100                 105                 110

<210> SEQ ID NO 109
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

```
Tyr Met His Trp Val Arg Gln Ala Pro Gly Gln Gly Leu Glu Trp Met
        35                  40                  45

Gly Val Ile Asn Pro Ser Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Asp Leu Ser Ser Leu Arg Ser Glu Asp Thr Ala Val Tyr Tyr Cys
                 85                  90                  95

Ala Arg Arg Ser Glu Ala Tyr Tyr His Gly Met Asp Val Trp Gly Gln
                100                 105                 110

Gly Thr Thr Val Thr Val Ser Ser
                115                 120

<210> SEQ ID NO 110
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu
                100                 105                 110

<210> SEQ ID NO 111
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Val Lys Pro Gly Glu
 1               5                  10                  15

Ser Leu Arg Leu Ser Cys Ala Ala Ser Gly Phe Thr Phe Lys Ser Tyr
                 20                  25                  30

Pro Met Ala Trp Val Arg Gln Ala Pro Gly Lys Gly Leu Glu Trp Val
             35                  40                  45

Ser Ser Ile Ser Ser Ser Gly Asp His Arg Tyr Tyr Ala Asp Ser Val
 50                  55                  60

Lys Gly Arg Phe Thr Ile Ser Arg Asp Asn Ala Arg Asn Ser Leu Ser
 65                  70                  75                  80

Leu Gln Met Asn Asn Leu Arg Ala Glu Asp Thr Ala Val Tyr Tyr Cys
                 85                  90                  95
```

-continued

Pro Ala Gly Arg Asp Phe Asp His Trp Gly Arg Gly Thr Leu Val Thr
                100                 105                 110
Val Ser Ser
        115

<210> SEQ ID NO 112
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Val Met Thr Gln Thr Pro Leu Ser Leu Pro Val Thr Pro Gly
1               5                   10                  15
Glu Pro Ala Ser Ile Ser Cys Arg Ser Ser Gln Ser Leu Leu Tyr Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Trp Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Ile Tyr Tyr Cys Met Gln Ala
                85                  90                  95
Leu His Val Pro Pro Tyr Thr Phe Gly Gln Gly Thr Lys Val Glu Ile
                100                 105                 110
Lys

<210> SEQ ID NO 113
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Glu Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Ile His Trp Val Arg Gln Ala Pro Gly Gln Gly Leu Glu Trp Val
        35                  40                  45
Gly Trp Ile Asn Pro Asn Ser Gly Gly Thr Asn Tyr Ala Gln Arg Phe
    50                  55                  60
Gln Gly Arg Val Thr Met Thr Arg Asp Thr Ser Ile Ser Thr Thr Tyr
65                  70                  75                  80
Met Glu Leu Ser Arg Leu Arg Phe Asp Asp Thr Ala Val Tyr Tyr Cys
                85                  90                  95
Ala Ser Asp Pro Gly Gly Asn Pro Tyr Phe Asp Tyr Trp Gly Gln Gly
                100                 105                 110
Thr Leu Val Thr Val Ser Ser
        115

<210> SEQ ID NO 114
<211> LENGTH: 106

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ser Tyr Glu Leu Thr Gln Pro Pro Ser Val Ser Val Ala Pro Gly Lys
1               5                   10                  15

Thr Ala Thr Ile Thr Cys Gly Gly Asp Thr Ile Gly Ser Lys Val Val
            20                  25                  30

His Trp Tyr Gln Gln Lys Pro Gly Gln Ala Pro Val Leu Val Met Tyr
        35                  40                  45

Tyr Asp Ser Glu Arg Pro Ser Gly Ile Pro Glu Arg Phe Ser Ala Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ser Val Val
                85                  90                  95

Phe Gly Gly Gly Thr Lys Leu Thr Val Leu
            100                 105

<210> SEQ ID NO 115
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Thr Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ser Glu Asp Thr Ala Leu Tyr Tyr Cys
                85                  90                  95

Ala Ser Asn His Asp Ile Leu Thr Gly Gly Asp Tyr Trp Gly Gln Gly
            100                 105                 110

Thr Leu Val Thr Val Ser Ser
        115

<210> SEQ ID NO 116
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Pro Tyr
```

```
                20                  25                  30
Ser Ile Asn Trp Tyr Gln Gln Leu Pro Gly Thr Ala Pro Lys Leu Leu
            35                  40                  45

Ile His Ser Asn Thr Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Val Val Phe Gly Gly Gly Thr Gln Leu Thr Val Leu
            100                 105                 110

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Val Glu Ser Gly Gly Ala Leu Val Gln Pro Gly Gly
1               5                   10                  15

Ser Leu Arg Leu Ser Cys Ala Gly Ser Gly Phe Thr Phe Ser Asn Phe
            20                  25                  30

Trp Met His Trp Val Arg Gln Ala Pro Gly Lys Gly Leu Glu Trp Val
        35                  40                  45

Ala Asp Ile Ser Gly Asp Gly Ser Glu Lys Tyr Tyr Val Asp Ser Val
    50                  55                  60

Lys Gly Arg Phe Thr Phe Ser Arg Asp Asn Ala Arg Asn Ser Leu Tyr
65                  70                  75                  80

Leu Gln Met Asn Ser Leu Arg Ile Glu Asp Thr Ala Val Tyr Tyr Cys
                85                  90                  95

Ala Arg Asp Ala Met Arg Gly Gly Asp Leu Asp Tyr Trp Gly Gln Gly
            100                 105                 110

Thr Leu Val Thr Val Ser Ser
        115

<210> SEQ ID NO 118
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro His
```

```
                    85                  90                  95

Phe Gly Gly Gly Thr Lys Val Glu Ile Lys
            100                 105

<210> SEQ ID NO 119
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Arg Phe Asp Tyr Tyr Asp Ser Ser Gly Tyr Tyr Tyr Gly Pro
            100                 105                 110

Phe Asp Tyr Trp Gly Gln Gly Thr Leu Val Thr Val Ser Ser
        115                 120                 125

<210> SEQ ID NO 120
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ser Val Val Thr Gln Pro Pro Ser Val Ser Ala Ala Pro Gly His
1               5                   10                  15

Lys Val Thr Ile Ser Cys Ser Gly Asn Ser Ser Asn Val Gly Arg Asn
            20                  25                  30

Tyr Val Ser Trp Tyr Gln Gln Val Pro Gly Thr Ala Pro Lys Leu Leu
        35                  40                  45

Ile Tyr Asp Asp Asn Lys Arg Pro Ser Gly Ile Pro Asp Arg Phe Ser
    50                  55                  60

Gly Ser Gln Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Thr Leu Tyr Val Phe Gly Thr Gly Thr Lys Leu Thr Val Leu
            100                 105                 110

<210> SEQ ID NO 121
<211> LENGTH: 124
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 121

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Leu Ser Ala Asp Lys Ser Thr Ser Thr Ala Tyr
65                  70                  75                  80

Val Gln Trp Asn Ser Leu Lys Ala Ser Asp Thr Ala Val Tyr Tyr Cys
                85                  90                  95

Ala Arg Leu Thr Val Ser Gly Ser Ser Thr Thr Thr Gly Gly Met Asp
            100                 105                 110

Val Trp Gly His Gly Thr Thr Val Thr Val Ser Ser
        115                 120
```

<210> SEQ ID NO 122
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Gln Ser Val Val Thr Gln Pro Pro Ser Val Ser Ala Ala Pro Gly Gln
1               5                   10                  15

Lys Val Thr Ile Ser Cys Ser Gly Ser Asp Ser Asn Ile Gly Asn Asn
            20                  25                  30

Tyr Val Ser Trp Tyr Gln Gln Val Pro Gly Thr Ala Pro Lys Leu Leu
        35                  40                  45

Ile Tyr Asp Asn Tyr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Val Thr Gly Asp Gly Gly Leu
                85                  90                  95

Gly Ala Val Val Phe Gly Gly Gly Thr Lys Leu Thr Val Leu
            100                 105                 110
```

<210> SEQ ID NO 123
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Asn Phe Asn Thr Tyr
            20                  25                  30

Tyr Ile His Trp Val Arg Gln Ala Pro Gly Gln Gly Leu Glu Trp Met
        35                  40                  45
```

```
Gly Ile Ile Asn Pro Ser Gly Gly Tyr Thr Ser Tyr Ala Gln Asn Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Leu Tyr Tyr Cys
                85                  90                  95

Ala Arg Glu Leu Gly Gly Asn Val Arg Arg Asp Asp Ala Phe Asp Ile
            100                 105                 110

Trp Gly Gln Gly Thr Met Val Thr Val Ser Ser
            115                 120

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Arg Tyr Tyr Ala
             20                  25                  30

Ser Trp Tyr Gln Gln Lys Pro Gly Gln Ala Pro Leu Leu Val Met Phe
         35                  40                  45

Gly Glu Asp Lys Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Thr Ser Gly Ser Trp
                85                  90                  95

Val Phe Gly Gly Gly Thr Lys Leu Thr Val Leu
            100                 105

<210> SEQ ID NO 125
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Met Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Leu His Trp Val Arg Gln Ala Pro Gly Gln Gly Leu Glu Trp Met
         35                  40                  45

Gly Ile Ile His Ser Ser Gly Ser Thr Thr Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Tyr Phe Gly Ser Gly Ser Phe Asp Tyr Trp Gly His Gly
            100                 105                 110
```

<210> SEQ ID NO 126
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
            100                 105                 110
```

<210> SEQ ID NO 127
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Gln Val Gln Leu Val Gln Ser Gly Ala Glu Val Lys Gln Pro Gly Ala
1               5                   10                  15

Ser Val Lys Val Ser Cys Lys Ala Ser Gly Tyr Thr Phe Thr Asn Asn
            20                  25                  30

Tyr Met His Trp Val Arg Gln Ala Pro Gly Gln Gly Leu Glu Trp Met
        35                  40                  45

Gly Ile Ile Asn Pro Thr Gly Gly Ser Thr Thr Tyr Ala Gln Lys Phe
50                  55                  60

Gln Gly Arg Val Ile Met Thr Thr Asp Thr Ser Thr Ser Thr Val Phe
65                  70                  75                  80

Met Glu Leu Ser Ser Leu Arg Ser Glu Asp Thr Ala Val Tyr Tyr Cys
                85                  90                  95

Ala Arg Asp Leu Gly Glu Leu Leu Ala Phe Asp Tyr Trp Gly Gln
            100                 105                 110

Gly Thr Leu Val Thr Val Ser Ser
            115                 120
```

<210> SEQ ID NO 128
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ser Tyr Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Thr Gly Thr Lys Val Thr Val Leu
            100                 105                 110

<210> SEQ ID NO 129
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Gly Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 130
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Gly Met Lys Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
         50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Leu Trp Gly Gln
            100                 105                 110

Gly Thr Leu Val Thr Val Ser Ser
        115                 120

<210> SEQ ID NO 131
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Gln Met Arg Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 132
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Leu Met Gln Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

-continued

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 133
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Glu Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 134
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Met Pro Asp Gly Tyr
            20                  25                  30

Tyr Met His Trp Val Arg Gln Ala Pro Gly Gln Gly Leu Glu Trp Met
        35                  40                  45

Gly Trp Ile Asn Pro Arg Thr Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Ala Phe Arg Leu Glu Leu Asp Ala Trp Gly Gln
            100                 105                 110

Gly Thr Leu Val Thr Val Ser Ser
        115                 120

<210> SEQ ID NO 135
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Arg Leu Gln Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 136
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Asn Trp Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Met Ala Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Ala Arg Gly Val Glu Leu Asp Met Trp Gly Gln
            100                 105                 110

Gly Thr Leu Val Thr Val Ser Ser
        115                 120

<210> SEQ ID NO 137
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Met Gln Leu Val Gln Ser Gly Ala Glu Val Lys Lys Pro Gly Ala
```

```
                1               5                  10                 15
Ser Val Lys Val Ser Cys Lys Ala Ser Gly Tyr Ser Phe Thr Gly Tyr
                20                 25                 30

Tyr Met His Trp Val Arg Gln Ala Pro Gly Gln Gly Leu Glu Trp Met
                35                 40                 45

Gly Trp Val Asn Pro Lys Ser Gly Gly Thr Asn Tyr Ala Gln Lys Phe
        50                 55                 60

Gln Gly Arg Val Thr Ile Thr Arg Asp Thr Ser Ala Ser Thr Ala Tyr
65                  70                 75                  80

Met Glu Leu Ser Ser Leu Arg Ser Glu Asp Thr Ala Val Tyr Tyr Cys
                85                 90                 95

Ala Arg Glu Gly Trp Ala Arg Arg Ile Asp Leu Asp Glu Trp Gly Gln
                100                105                110

Gly Thr Leu Val Thr Val Ser Ser
                115                120

<210> SEQ ID NO 138
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Met Gln Leu Val Gln Ser Gly Ala Glu Val Lys Lys Pro Gly Ala
1               5                  10                 15

Ser Val Lys Val Ser Cys Lys Ala Ser Gly Tyr Ser Phe Ser Gly Tyr
                20                 25                 30

Tyr Met His Trp Val Arg Gln Ala Pro Gly Gln Gly Leu Glu Trp Met
                35                 40                 45

Gly Trp Val Asn Pro Met Ser Gly Gly Thr Asn Tyr Ala Gln Lys Phe
        50                 55                 60

Gln Gly Arg Val Thr Ile Thr Arg Asp Thr Ser Ala Ser Thr Ala Tyr
65                  70                 75                  80

Met Glu Leu Ser Ser Leu Arg Ser Glu Asp Thr Ala Val Tyr Tyr Cys
                85                 90                 95

Ala Arg Glu Gly Met Ala Met Arg Leu Glu Leu Asp Lys Trp Gly Gln
                100                105                110

Gly Thr Leu Val Thr Val Ser Ser
                115                120

<210> SEQ ID NO 139
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Met Gln Leu Val Gln Ser Gly Ala Glu Val Lys Lys Pro Gly Ala
1               5                  10                 15

Ser Val Lys Val Ser Cys Lys Ala Ser Gly Tyr Asn Phe Ala Gly Tyr
                20                 25                 30

Tyr Met His Trp Val Arg Gln Ala Pro Gly Gln Gly Leu Glu Trp Met
                35                 40                 45

Gly Trp Val Asn Pro Gln Ser Gly Gly Thr Asn Tyr Ala Gln Lys Phe
```

```
                    50                  55                  60
Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Glu Gly Gly Arg Gly Leu Asp Leu Asp Trp Trp Gly Gln
                100                 105                 110

Gly Thr Leu Val Thr Val Ser Ser
            115                 120

<210> SEQ ID NO 140
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Met Gln Leu Val Gln Ser Gly Ala Glu Val Lys Lys Pro Gly Ala
 1               5                  10                  15

Ser Val Lys Val Ser Cys Lys Ala Ser Gly Tyr Asn Phe Ser Gly Tyr
                20                  25                  30

Tyr Met His Trp Val Arg Gln Ala Pro Gly Gln Gly Leu Glu Trp Met
            35                  40                  45

Gly Trp Ile Asn Pro Lys Ser Gly Gly Thr Asn Tyr Ala Gln Lys Phe
        50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Gly Gly Ala Arg Gly Val Asp Leu Asp Thr Trp Gly Gln
                100                 105                 110

Ala Thr Leu Val Thr Val Ser Ser
            115                 120

<210> SEQ ID NO 141
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Met Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Gly Gly Tyr
                20                  25                  30

Tyr Met His Trp Val Arg Gln Ala Pro Gly Gln Gly Leu Glu Trp Met
            35                  40                  45

Gly Trp Val Asn Pro Asn Ser Gly Gly Thr Asn Tyr Ala Gln Lys Phe
        50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Gly Tyr Gly Leu Gly Leu Asp Leu Asp Val Trp Gly Gln
```

```
                100                 105                 110

Gly Thr Leu Val Thr Val Ser Ser
        115                 120

<210> SEQ ID NO 142
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Gly Gly Tyr
            20                  25                  30

Tyr Met His Trp Val Arg Gln Ala Pro Gly Gln Gly Leu Glu Trp Met
        35                  40                  45

Gly Trp Val Asn Pro Lys Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Val Gly Leu Asp Leu Asp Tyr Trp Gly Gln
            100                 105                 110

Gly Thr Leu Val Thr Val Ser Ser
        115                 120

<210> SEQ ID NO 143
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Gly Gly Tyr
            20                  25                  30

Tyr Met His Trp Val Arg Gln Ala Pro Gly Gln Gly Leu Glu Trp Met
        35                  40                  45

Gly Trp Val Asn Pro His Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Ala Trp Gly Leu Asp Leu Asp Leu Trp Gly Gln
            100                 105                 110

Gly Thr Leu Val Thr Val Ser Ser
        115                 120

<210> SEQ ID NO 144
<211> LENGTH: 4
<212> TYPE: PRT
```

```
<213> ORGANISM: Unknown
<220> FEATURE:
<223> OTHER INFORMATION: Description of Unknown:
      Hinge region sequence

<400> SEQUENCE: 144

Cys Pro Ser Cys
1

<210> SEQ ID NO 145
<211> LENGTH: 4
<212> TYPE: PRT
<213> ORGANISM: Unknown
<220> FEATURE:
<223> OTHER INFORMATION: Description of Unknown:
      Hinge region sequence

<400> SEQUENCE: 145

Cys Pro Pro Cys
1
```